US011636616B2

(12) United States Patent
Ebata

(10) Patent No.: US 11,636,616 B2
(45) Date of Patent: *Apr. 25, 2023

(54) ACOUSTIC WAVE DIAGNOSTIC APPARATUS AND CONTROL METHOD OF ACOUSTIC WAVE DIAGNOSTIC APPARATUS

(71) Applicant: FUJIFILM Corporation, Tokyo (JP)

(72) Inventor: Tetsurou Ebata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 62 days.

This patent is subject to a terminal disclaimer.

(21) Appl. No.: 17/496,647

(22) Filed: Oct. 7, 2021

(65) Prior Publication Data

US 2022/0028104 A1 Jan. 27, 2022

Related U.S. Application Data

(63) Continuation of application No. 16/825,909, filed on Mar. 20, 2020, now Pat. No. 11,170,519, which is a (Continued)

(30) Foreign Application Priority Data

Oct. 17, 2017 (JP) .............................. JP2017-200857

(51) Int. Cl.
*G06K 9/00* (2022.01)
*A61B 5/02* (2006.01)
(Continued)

(52) U.S. Cl.
CPC .............. *G06T 7/62* (2017.01); *A61B 8/085* (2013.01); *A61B 8/0891* (2013.01); *A61B 8/14* (2013.01);
(Continued)

(58) Field of Classification Search
CPC .................................... A61B 5/02; G06K 9/00
(Continued)

(56) References Cited

U.S. PATENT DOCUMENTS

2010/0036248 A1 2/2010 Chouno
2012/0179042 A1* 7/2012 Fukumoto ............ A61B 8/0891
600/443

(Continued)

FOREIGN PATENT DOCUMENTS

CN 101522107 A 9/2009
CN 102469987 A 5/2012
(Continued)

OTHER PUBLICATIONS

An Office Action mailed by China National Intellectual Property Administration dated Apr. 29, 2022, which corresponds to Chinese Patent Application No. 201880066370.1 and is related to U.S. Appl. No. 17/496,647 with English language translation.

(Continued)

*Primary Examiner* — Seyed H Azarian
(74) *Attorney, Agent, or Firm* — Studebaker & Brackett PC

(57) ABSTRACT

An ultrasound diagnostic apparatus includes an image memory, an operation unit, a measurement item designation receiving unit for receiving a designation of a measurement item, a detection measurement algorithm setting unit that sets a detection measurement algorithm, a frame designation receiving unit that receives a designation of a frame to be used for the measurement among a plurality of frames in the image memory, a measurement position designation receiving unit that receives a designation of a position of a measurement target on a first measurement frame received by the frame designation receiving unit, a measurement position setting unit that sets the position of the measure- (Continued)

ment target on a frame other than the first measurement frame, a measurement unit that detects the measurement target on the plurality of frames to calculate the measurement value, and a final measurement value calculation unit that calculates a final measurement value.

16 Claims, 17 Drawing Sheets

Related U.S. Application Data continuation of application No. PCT/JP2018/037644, filed on Oct. 10, 2018.

(51) Int. Cl.
    *G06T 7/62*           (2017.01)
    *A61B 8/08*           (2006.01)
    *A61B 8/14*           (2006.01)
    *A61B 8/00*           (2006.01)
    *G06T 7/00*           (2017.01)
    *G06T 7/20*           (2017.01)

(52) U.S. Cl.
    CPC .............. *A61B 8/463* (2013.01); *A61B 8/465* (2013.01); *A61B 8/5223* (2013.01); *G06T 7/0012* (2013.01); *G06T 7/20* (2013.01); *G06T 2207/10016* (2013.01); *G06T 2207/10132* (2013.01)

(58) Field of Classification Search
    USPC ......... 382/100, 103, 106, 128–13, 154, 172, 382/168, 173, 181, 189, 199, 209, 219, 382/224, 254, 276, 285–291, 305, 312; 367/135; 600/442, 443, 479
    See application file for complete search history.

(56) References Cited

U.S. PATENT DOCUMENTS

| | | | | |
|---|---|---|---|---|
| 2013/0123628 A1* | 5/2013 | Katsuyama | .......... | A61B 8/0858 600/442 |
| 2013/0150721 A1 | 6/2013 | Kawabata et al. | | |
| 2016/0139251 A1* | 5/2016 | Imai | .......... | G01H 3/00 367/135 |
| 2016/0331242 A1* | 11/2016 | Irisawa | ............... | A61B 8/0841 |
| 2020/0008775 A1* | 1/2020 | Erkamp | ............... | A61B 5/065 |
| 2020/0163612 A1* | 5/2020 | Ntziachristos | ......... | A61B 5/489 |

FOREIGN PATENT DOCUMENTS

| | | |
|---|---|---|
| EP | 2 072 013 A1 | 6/2009 |
| JP | 2000-152936 A | 6/2000 |
| JP | 2004-121835 A | 4/2004 |
| JP | 2010-140425 A | 6/2010 |
| JP | 2016-097256 A | 5/2016 |
| JP | 2017-143969 A | 8/2017 |
| WO | 2011/099103 A1 | 8/2011 |
| WO | 2017/158897 A1 | 9/2017 |

OTHER PUBLICATIONS

International Search Report issued in PCT/JP2018/037644; dated Dec. 4, 2018.
International Preliminary Report on Patentability and Written Opinion issued in PCT/JP2018/037644; dated Apr. 21, 2020.
Yasuki Kihara et al.; "Standard Measurement of Cardiac Function Indexes"; The Terminology and Diagnostic Criteria Committee of The Japan Society of Ultrasonics in Medicine; J. Med Ultrasonics vol. 33 No. 3; May 2006 pp. 371-381 (English language translation on pp. 376-381); Japan.
An Office Action; "Notice of Reasons for Refusal", mailed by the Japanese Patent Office dated Jan. 26, 2021, which corresponds to Japanese Patent Application No. 2019-549217 and is related to U.S. Appl. No. 16/825,909; with English language translation.
The extended European search report issued by the European Patent Office dated Nov. 20, 2020, which corresponds to European Patent Application No. 18868545.7-1122 and is related to U.S. Appl. No. 16/825,909.
An Office Action mailed by China National Intellectual Property Administration dated Oct. 13, 2022, which corresponds to Chinese Patent Application No. 201880066370.1 and is related to U.S. Appl. No. 17/496,647; with English language translation.
John C. McEachen II et al., "Shape-Based Tracking of Left Ventricular Wall Motion", IEEE Transactions on Medical maging, vol. 16, No. 3, Jun. 1, 1997, pp. 270-283, IEEE, USA.
McNally D. et al., "Computer Vision Elastography: Speckle Adaptive Motion Estimation for Elastography Using Ultrasound Sequences", IEEE Transactions on Medical Imaging, vol. 24, No. 6, Jun. 1, 2005, pp. 755-766, IEEE, USA.
Revell J. D. et al., "Musculoskeletal motion flow fields using hierarchical variable-sized block matching in ultrasonographic video sequences", Journal of Biomechanics, vol. 37, No. 4, Jan. 1, 2004, pp. 511-522, Elsevier.
Djamal Boukerroui et al., "Velocity Estimation in Ultrasound Images: A Block Matching Approach", In: Lecture Notes in Computer Science, vol. 2732, Jan. 1, 2003, pp. 586-598, Springer, Berlin, Heidelberg.
Communication pursuant to Article 94(3) EPC issued by the European Patent Office dated Feb. 14, 2023, which corresponds to European Patent Application No. 18868545.7-1126 and is related to U.S. Appl. No. 17/496,647.

* cited by examiner

ACOUSTIC WAVE DIAGNOSTIC APPARATUS AND CONTROL METHOD OF ACOUSTIC WAVE DIAGNOSTIC APPARATUS

CROSS-REFERENCE TO RELATED APPLICATIONS

This application is a Continuation of U.S. application Ser. No. 16/825,909 filed on Mar. 20, 2020, which claims priority under 35 U.S.C § 119(a) to PCT International Application No. PCT/JP2018/037644 filed on Oct. 10, 2018, and Japanese Patent Application No. 2017-200857 filed on Oct. 17, 2017. Each of the above application(s) is hereby expressly incorporated by reference, in its entirety, into the present application.

BACKGROUND OF THE INVENTION

1. Field of the Invention

The present invention relates to an acoustic wave diagnostic apparatus and a control method of an acoustic wave diagnostic apparatus and in particular, to an acoustic wave diagnostic apparatus and a control method of an acoustic wave diagnostic apparatus for measuring a part on an acoustic wave image.

2. Description of the Related Art

In recent years, a medical acoustic wave diagnostic apparatus generally has a measurement function of measuring a length, an area, and the like of a measurement target such as a part included in an acquired acoustic wave image. In a case of measuring a measurement target using such an acoustic wave diagnostic apparatus, a user sometimes performs a measurement on acoustic wave images of a plurality of frames in accordance with diagnostic contents. In this case, in general, since the user manually performs a measurement operation for each of the plurality of frames, a burden on the user is increased as compared with a case of performing a measurement on one frame. Therefore, in order to reduce the burden on the user in a case of performing a measurement on acoustic wave images of a plurality of frames, various attempts to automate operations performed by the user are made.

For example, in JP2004-121835A, there is disclosed an ultrasound diagnostic apparatus that automatically sets a region of interest for a plurality of frames by causing the region of interest to sequentially follow to a frame adjacent in time series from a frame in which the user has set the region of interest, in a case where the user sets the region of interest for one frame among a plurality of frames continuous in time series. Further, the ultrasound diagnostic apparatus of JP2004-121835A calculates an index value such as an average value of luminance in a region of interest imparted with respect to a plurality of frames to obtain a highly reliable index value even in a case where a tissue of a subject has been moved.

SUMMARY OF THE INVENTION

By the way, in the measurement using an ultrasound image, a measurement method may differ depending on a measurement target, for example, a measurement of a length and a measurement of an area of the measurement target. Since the ultrasound diagnostic apparatus disclosed in JP2004-121835A cannot automatically determine a measurement method corresponding to a measurement target, in a case where a measurement is performed on the measurement target, the user sometimes determines a measurement method corresponding to a measurement target, which causes an increase in a burden on a user.

Further, in the ultrasound diagnostic apparatus disclosed in JP2004-121835A, in a case of calculating a final measurement value based on a plurality of measurement values in a plurality of frames, the user sometimes determines a measurement method corresponding to the measurement target and performs measurement operations for each of the plurality of frames, which is a problem in that the burden on the user is further increased.

The present invention has been made in order to solve such a conventional problem, and it is an object of the present invention to provide an acoustic wave diagnostic apparatus capable of reducing a burden on a user and easily obtaining a final measurement value and a control method of an acoustic wave diagnostic apparatus.

In order to achieve the aforementioned object, an acoustic wave diagnostic apparatus according to an aspect of the present invention comprises: an image memory that stores acoustic wave images of a plurality of frames continuous in time series; a display unit that displays the acoustic wave images; an operation unit for a user to perform an input operation; a measurement item designation receiving unit that receives a designation of a measurement item related to a measurement target from the user through the operation unit; a detection measurement algorithm setting unit that sets a detection measurement algorithm based on the measurement item received by the measurement item designation receiving unit; a frame designation receiving unit that receives a designation of a measurement frame to be used for a measurement among the plurality of frames stored in the image memory from the user through the operation unit; a measurement position designation receiving unit that receives a designation of a position of the measurement target on an acoustic wave image of a first measurement frame received by the frame designation receiving unit and displayed on the display unit; a measurement position setting unit that calculates a movement amount of the acoustic wave images between the plurality of frames, and sets the position of the measurement target in a frame other than the first measurement frame among the plurality of frames based on the movement amount and the position of the measurement target received by the measurement position designation receiving unit; a measurement unit that detects the measurement target from the acoustic wave image for each of the plurality of frames based on the position of the measurement target received by the measurement position designation receiving unit, the position of the measurement target set by the measurement position setting unit and the detection measurement algorithm set by the detection measurement algorithm setting unit, and measures the detected measurement target and displays a plurality of measurement values in the plurality of frames on the display unit; and a final measurement value calculation unit that calculates a final measurement value from a first measurement value calculated by the measurement unit for the first measurement frame and a second measurement value in a second measurement frame set based on the plurality of measurement values for the plurality of frames, among the plurality of measurement values.

An acoustic wave diagnostic apparatus according to another aspect of the present invention can further comprise a reliability calculation unit that calculates a reliability of the measurement value in each of the plurality of frames and displays the calculated reliability on the display unit.

In the acoustic wave diagnostic apparatus according to the other aspect of the present invention, the second measurement frame can be designated by the user through the operation unit and can be received by the frame designation receiving unit.

In addition, the acoustic wave diagnostic apparatus according to the other aspect of the present invention can further comprise a second measurement frame setting unit that automatically sets the second measurement frame from among the plurality of frames based on the measurement value acquired by the measurement unit and the reliability calculated by the reliability calculation unit.

Further, in the acoustic wave diagnostic apparatus according to the other aspect of the present invention, in a case where the measurement value in the first measurement frame is a value obtained by measuring one of a maximum value and a minimum value, the second measurement frame setting unit can set a frame which is the other of the maximum value and the minimum value from a plurality of measurement values in the plurality of frames as the second measurement frame.

Further, in the acoustic wave diagnostic apparatus according to the other aspect of the present invention, the measurement position setting unit sequentially detects positions of a follow-up region of interest set on the acoustic wave images with respect to adjacent frames to calculate the movement amount of the acoustic wave images between the plurality of frames.

Further, the acoustic wave diagnostic apparatus according to the other aspect of the present invention can further comprise a measurement frame selection unit that selects a part of frames for detecting and measuring the measurement target by the measurement unit from among the plurality of frames.

Further, in the acoustic wave diagnostic apparatus according to the other aspect of the present invention, the measurement frame selection unit can select a frame group from the first measurement frame to a newest frame among the plurality of frames as the part of frames in a case where the first measurement frame is positioned in a first half of the plurality of frames in time series, and select a frame group from an oldest frame among the plurality of frames to the first measurement frame as the part of frames in a case where the first measurement frame is positioned in a second half of the plurality of frames in time series.

Furthermore, in the acoustic wave diagnostic apparatus according to the other aspect of the present invention, it is preferable that the measurement position setting unit sets the position of the measurement target only for the part of frames selected by the measurement frame selection unit.

Further, in the acoustic wave diagnostic apparatus according to the other aspect of the present invention, the detection measurement algorithm setting unit determines whether the measurement item received by the measurement item designation receiving unit requests only measurement for a single frame or requests a measurement for a plurality of frames, and in the case of requesting only measurement for the single frame, the detection measurement algorithm setting unit can cause the measurement unit to display a measurement value for the first measurement frame on the display unit, and then end the detection and measurement of the measurement target.

A control method of an acoustic wave diagnostic apparatus according to an aspect of the present invention comprises: storing acoustic wave images of a plurality of frames continuous in time series; displaying the acoustic wave images; receiving a designation of a measurement item related to a measurement target from a user through an operation unit; setting a detection measurement algorithm based on the received measurement item; receiving a designation of a first measurement frame to be used for a measurement among the plurality of stored frames from the user through the operation unit; receiving a designation of a position of the measurement target on the displayed acoustic wave image of the first measurement frame; receiving a designation of a position of the measurement target on a displayed acoustic wave image of a first measurement frame; calculating a movement amount of the acoustic wave images between the plurality of frames, and setting a position of the measuring target in a frame other than the first measurement frame among the measurement frames based on the position of the measurement target in the received first measurement frame and the movement amount; detecting the measurement target from the acoustic wave image for each of the plurality of frames based on the position of the measurement target in the received first measurement frame, the position of the measurement target in the frame other than the set first measurement frame, and the set detection measurement algorithm; measuring the detected measurement target and displaying a plurality of measurement values in the plurality of frames; setting a second measurement frame based on the plurality of measurement values for the plurality of frames; and calculating a final measurement value from a first measurement value in the first measurement frame and a second measurement value in the second measurement frame among the plurality of measurement values.

According to the present invention, since an acoustic wave diagnostic apparatus comprises a measurement unit that detects a measurement target from an acoustic wave image for each of a plurality of frames and measures the detected measurement target to display a plurality of measurement values in the plurality of frames on a display unit based on a position of the measurement target received by a measurement position designation receiving unit, a position of the measurement target set by a measurement position setting unit, and a detection measurement algorithm set by a detection measurement algorithm setting unit, and a final measurement value calculation unit that calculates a final measurement value from a first measurement value calculated by the measurement unit in the first measurement frame and a second measurement value in a second measurement frame set based on the plurality of measurement values in the plurality of frames, among the plurality of measurement values, it is possible to easily obtain a final measurement value while reducing a burden on a user.

DESCRIPTION OF THE PREFERRED EMBODIMENTS

Hereinafter, embodiments of the present invention will be described with reference to the accompanying diagrams.

First Embodiment

Figure 1:
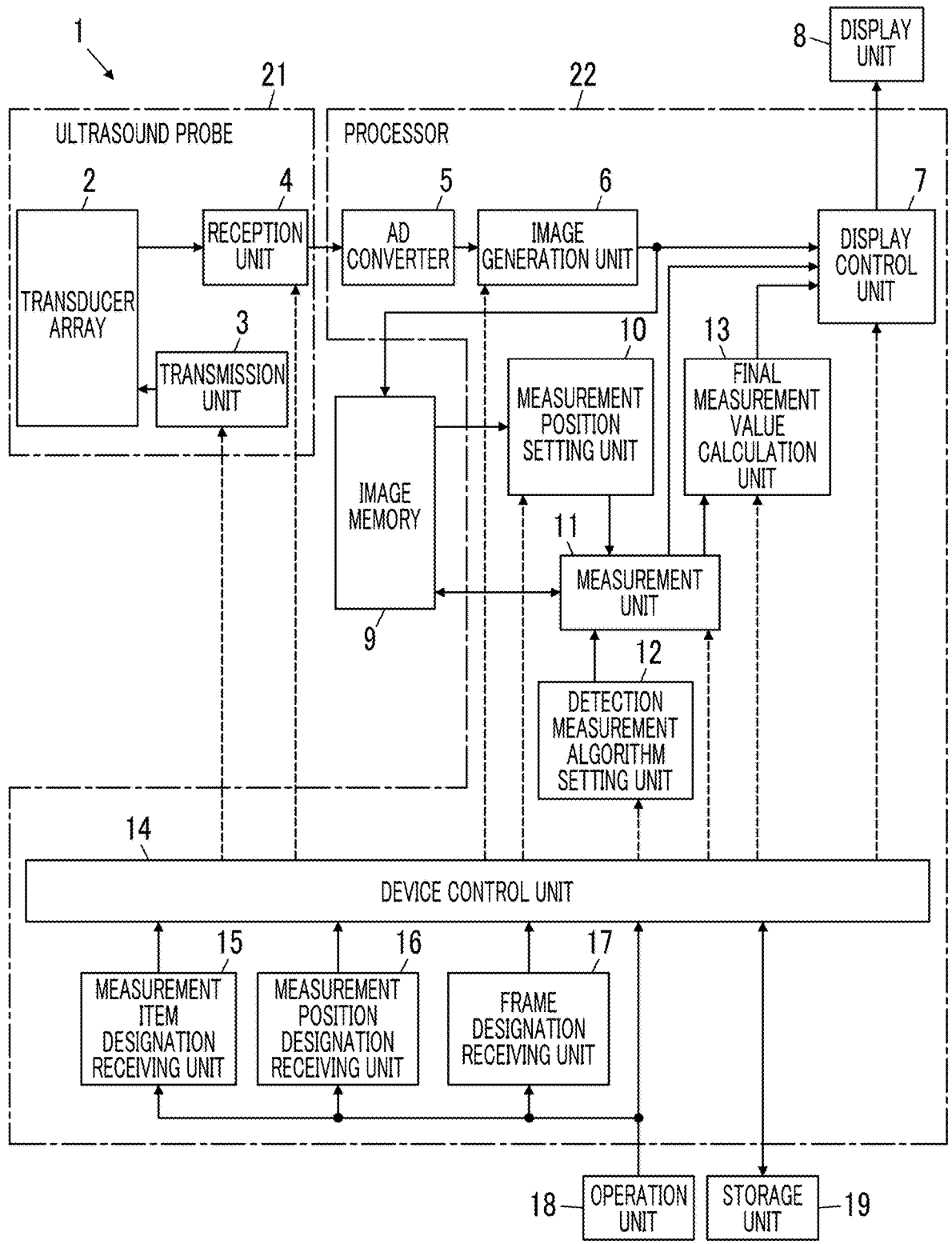
FIG. 1 is a block diagram showing a configuration of an ultrasound diagnostic apparatus according to a first embodiment of the present invention.

FIG. 1 shows a configuration of an ultrasound diagnostic apparatus 1 according to a first embodiment of the present invention. As shown in FIG. 1, the ultrasound diagnostic apparatus 1 comprises a transducer array 2, and a transmission unit 3 and a reception unit 4 are connected to the transducer array 2. An analog digital (AD) converter 5, an image generation unit 6, a display controller 7, and a display unit 8 are sequentially connected to the reception unit 4. Further, an image memory 9 is connected to the image generation unit 6, and a measurement position setting unit 10 is connected to the image memory 9. Further, a measurement unit 11 is connected to the image memory 9 and the measurement position setting unit 10, and a detection measurement algorithm setting unit 12 and a final measurement value calculation unit 13 are connected to the measurement unit 11, respectively.

Further, the device controller 14 is connected to the transmission unit 3, the reception unit 4, the image generation unit 6, the display controller 7, the measurement position setting unit 10, the measurement unit 11, the detection measurement algorithm setting unit 12, and the final measurement value calculation unit 13. Further, a measurement item designation receiving unit 15, a measurement position designation receiving unit 16, a frame designation receiving unit 17, an operation unit 18, and a storage unit 19 are connected to the device controller 14. The measurement item designation receiving unit 15, the measurement position designation receiving unit 16, and the frame designation receiving unit 17 are connected to the operation unit 18, respectively.

Note that, the image memory 9 and the measurement unit 11, and the device controller 14 and the storage unit 19 are connected to each other so that information can be transmitted and received bidirectionally.

Further, an ultrasound probe 21 is configured by the transducer array 2, the transmission unit 3, and the reception unit 4. Further, the processor 22 is configured by the AD converter 5, the image generation unit 6, the display controller 7, the measurement position setting unit 10, the measurement unit 11, the detection measurement algorithm setting unit 12, the final measurement value calculation unit 13, the device controller 14, the measurement item designation receiving unit 15, the measurement position designation receiving unit 16, and the frame designation receiving unit 17.

The transducer array 2 of the ultrasound probe 21 shown in FIG. 1 has a plurality of elements (ultrasound transducers) arranged in a one-dimensional or two-dimensional manner. According to a driving signal supplied from the transmission unit 3, each of the elements transmits an ultrasound wave and receives a reflected wave from a subject and outputs a reception signal. For example, each element is formed by using a transducer in which electrodes are formed at both ends of a piezoelectric body formed of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission unit 3 of the ultrasound probe 21 includes, for example, a plurality of pulse generators. Based on a transmission delay pattern selected according to the control signal from the device controller 14, the transmission unit 3 adjusts the amount of delay of each driving signal so that ultrasound waves transmitted from the plurality of elements of the transducer array 2 form an ultrasound beam, and supplies it to the plurality of elements. Thus, in a case where a pulsed or continuous-wave voltage is applied to the electrodes of the elements of the transducer array 2, the piezoelectric body expands and contracts to generate pulsed or continuous-wave ultrasound waves from each transducer. From the combined wave of these ultrasound waves, an ultrasound beam is formed.

The transmitted ultrasound beam is reflected by a target, for example, a part of the subject, and propagates toward the transducer array 2 of the ultrasound probe 21. The ultrasound waves propagating toward the transducer array 2 in this manner are received by the respective elements configuring the transducer array 2. In this case, the respective transducers configuring the transducer array 2 expand and contract by receiving the propagating ultrasound waves, thereby generating electric signals. These electric signals are output, as reception signals of the ultrasound waves, from each transducer to the reception unit 4. Although not shown, the reception unit 4 has an amplification unit for amplifying an ultrasound reception signal input from each transducer. In a case where the amplified signal is converted into digitized element data by the AD converter 5, the element data is output to the image generation unit 6.

Figure 2:
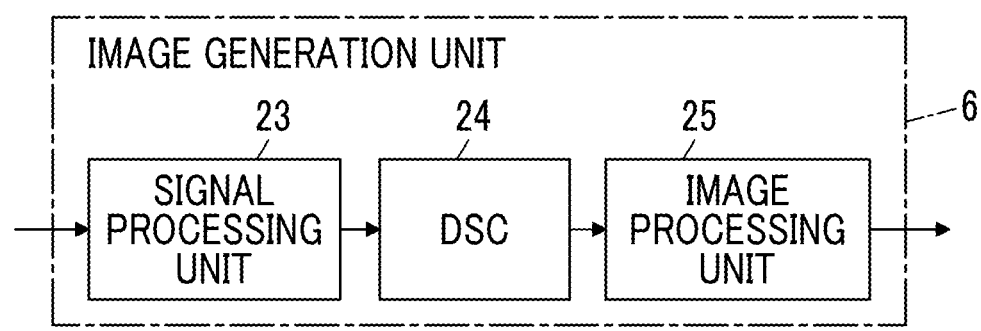
FIG. 2 is a block diagram showing an internal configuration of an image generation unit in the first embodiment of the present invention.

As shown in FIG. 2, the image generation unit 6 of the processor 22 has a configuration in which a signal processing unit 23, a digital scan converter (DSC) 24, and an image processing unit 25 are connected in series to each other. Based on a reception delay pattern selected according to the control signal from the device controller 14, the signal processing unit 23 performs reception focusing processing in which delays are given to respective pieces of element data according to the set sound speed and addition (phasing addition) is performed. Through the reception focusing processing, a sound ray signal with narrowed focus of the ultrasound echo is generated. Further, the signal processing unit 23 generates a B mode image signal, which is tomographic image information regarding tissues inside the subject, by correcting the attenuation of the generated sound ray signal due to the propagation distance according to the depth of the reflection position of the ultrasound wave and then performing envelope detection processing. The B mode image signal generated as described above is output to the DSC 24.

The DSC 24 raster-converts the B mode image signal into an image signal according to the normal television signal scanning method. The image processing unit 25 performs various kinds of necessary image processing, such as brightness correction, gradation correction, sharpness correction, and color correction, on the image data obtained in the DSC 24, and then outputs the B mode image signal to the display controller 7 and the image memory 9 under the control of the device controller 14. Hereinafter, the B-mode image signal is referred to as an ultrasound image.

The image memory 9 of the ultrasound diagnostic apparatus 1 is for storing an ultrasound image and recording media, such as a hard disc drive (HDD), a solid state drive (SSD), a flexible disc (FD), a magneto-optical disc (MO), a magnetic tape (MT), a random access memory (RAM), a compact disc (CD), a digital versatile disc (DVD), a secure digital card (SD card), and a universal serial bus memory (USB memory), or a server can be used. The image memory 9 can store an ultrasound image generated by the image generation unit 6 and can also store an ultrasound image input from an external device (not shown).

The measurement item designation receiving unit 15 of the processor 22 receives a designation of a measurement item relevant to the measurement target from the user through the operation unit 18. Here, the measurement item relevant to the measurement target is an item that can indicate at least one of the measurement target or the measurement content, and the measurement target can include a name of a target part such as an organ, a name of a lesion such as a tumor, a cyst, and a hemorrhage, and an item relevant to abnormalities. Therefore, for example, the measurement item can include any one of only the name of a measurement target, only the name of a lesion, only the item relevant to abnormalities, the name of a measurement target and its measurement content, the name of a lesion and its measurement content, or an item relevant to abnormalities and its measurement content. In a case where the measurement item includes only the measurement target, for example, the measurement content, such as whether the length is to be measured or the size is to be measured for the measurement target designated by the user through the operation unit 18, is associated therewith. Specifically, for example, a table in which the measurement target and the measurement content are associated with each other is stored in the storage unit 19, an external memory (not shown), or the like, and the measurement content corresponding to the measurement target is selected based on this table.

The measurement position designation receiving unit 16 of the processor 22 receives a designation of the position of the measurement target on the ultrasound image displayed on the display unit 8 from the user through the operation unit 18.

The frame designation receiving unit 17 of the processor 22 receives a designation of a measurement frame to be used for the measurement among a plurality of frames stored in the image memory 9 from the user through the operation unit 18.

The detection measurement algorithm setting unit 12 of the processor 22 sets an algorithm for detecting the measurement target and an algorithm for measuring the measurement target based on the measurement item that the measurement item designation receiving unit 15 has received from the user through the operation unit 18. The detection measurement algorithm setting unit 12 stores an algorithm corresponding to each measurement target and an algorithm corresponding to each measurement content as an association table, and sets a detection measurement algorithm with reference to the association table in a case where the measurement item designation receiving unit 15 receives a measurement item from the user through the operation unit 18.

Here, generally, different measurement rules exist for each measurement target. The measurement rule is a rule on, which part is measured and how it is measured for a specific measurement target. For example, in a case where the measurement target is an inferior vena cava diameter, there is a measurement rule of determining a line segment whose end points are two points on the inner wall of the inferior vena cava as a measurement line so as to be perpendicular to the traveling direction of the inferior vena cava, and measuring the determined length of the line segment. Further, for example, in a case where the measurement target is a kidney, there is a measuring rule of measuring a length between two points at which a distance becomes maximum among two points on a boundary of a kidney region included in the ultrasound image. The detection measurement algorithm defines calculation means for executing such a measurement rule, and differs for each measurement target.

Further, the algorithm defines calculation means for achieving the purpose, such as detection and measurement. For example, the algorithm is implemented as a software program in an apparatus and is executed by a central processing unit (CPU). As the detection measurement algorithm set by the detection measurement algorithm setting unit 12, a known algorithm that is generally used can be used.

For example, for the algorithm for detecting the measurement target, there is a method in which typical pattern data is stored in advance as a template, a pattern data similarity is calculated while searching for an image with a template, and it is considered that a measurement target is present in a place where the similarity is equal to or greater than a threshold value and is the maximum. For the calculation of the similarity, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

The measurement position setting unit 10 of the processor 22 sets the position of the measurement target with respect to the ultrasound images of the plurality of frames continuous in time series stored in the image memory 9. In this case, the measurement position setting unit 10 calculates a movement amount of the ultrasound images between the plurality of frames, and sets the position of the measurement target in the plurality of frames based on the calculated movement amount and the position of the measurement target received by the measurement position designation receiving unit 16. In this case, the measurement position setting unit 10 can set, for example, a region of interest with respect to the ultrasound images of the plurality of frames continuous in time series, and calculate the movement amount of the ultrasound images between the plurality of frames by sequentially detecting the set positions of the region of interest with respect to the frames adjacent in time series. A specific operation of setting the position of the measurement target by the measurement position setting unit 10 will be described later in detail.

The measurement unit 11 of the processor 22 detects a measurement target from the ultrasound image for each of the plurality of frames stored in the image memory 9, performs a measurement of the detected measurement target, and displays a plurality of measurement values in a plurality of frames on the display unit 8 through the display controller 7. At this time, the measurement unit 11 detects the measurement target from the ultrasound image based on the position of the measurement target received by the measurement position designation receiving unit 16, the position of the measurement target set by the measurement position setting unit 10, and the detection measurement algorithm set by the detection measurement algorithm setting unit 12. For example, specifically, the measurement unit 11 determines the position of the detection range for detecting the measurement target based on the position designated by the user through the operation unit 18 and the position of the measurement target set by the measurement position setting unit 10 and detects the measurement target within the determined detection range. The size of the detection range can be set in advance, and the setting can be changed by the user through the operation unit 18.

The final measurement value calculation unit 13 of the processor 22 calculates a final measurement value based on the plurality of measurement values calculated by the measurement unit 11. For example, in general, in a case where a diagnosis of heart failure is made, a value obtained by dividing the diameter of the inferior vena cava in the expiratory state by the diameter of the inferior vena cava in the inspiratory state is used as the final measurement value. Therefore, for example, in a case where the inferior vena cava diameter is selected as a measurement item by the user through the operation unit 18, the measurement unit 11 can calculate a value obtained by dividing the first measurement value by the second measurement value as a final measurement value from the measurement value in the first measurement frame of which measurement position is designated by the user through the operation unit 18 and the second measurement value in a second measurement frame set based on a plurality of measurement values for a plurality of frames.

The display controller 7 of the processor 22 causes the display unit 8 to display the ultrasound image generated by the image generation unit 6, the measurement value calculated by the measurement unit 11, the final measurement value calculated by the final measurement value calculation unit 13, and the like under the control of the device controller 14.

The display unit 8 of the ultrasound diagnostic apparatus 1 includes, for example, a display device, such as a liquid crystal display (LCD), and displays data such as an ultrasound image output from the display controller 7.

The device controller 14 of the processor 22 controls each unit of the ultrasound diagnostic apparatus 1 based on a command input by the user through the operation unit 18.

The operation unit 18 of the ultrasound diagnostic apparatus 1 is for the user to perform an input operation, and can be configured by comprising a keyboard, a mouse, a trackball, a touch pad, a touch panel, and the like.

The storage unit 19 of the ultrasound diagnostic apparatus 1 is for storing an operation program and the like of the ultrasound diagnostic apparatus 1 and recording media, such as: a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), or a server can be used.

The processor 22 including the AD converter 5, the image generation unit 6, the display controller 7, the measurement position setting unit 10, the measurement unit 11, the detection measurement algorithm setting unit 12, the final measurement value calculation unit 13, the device controller 14, the measurement item designation receiving unit 15, the measurement position designation receiving unit 16, and the frame designation receiving unit 17 is configured by a CPU and a control program for causing the CPU to perform various processes, but may be configured by using a digital circuit. Further, the AD converter 5, the image generation unit 6, the display controller 7, the measurement position setting unit 10, the measurement unit 11, the detection measurement algorithm setting unit 12, the final measurement value calculation unit 13, the device controller 14, the measurement item designation receiving unit 15, the measurement position designation receiving unit 16, and the frame designation receiving unit 17 can also be integrated partially or entirely into one CPU.

Next, the operation of the ultrasound diagnostic apparatus 1 according to the first embodiment will be described with reference to the flowchart shown in FIG. 3.

First, in step S1, the measurement item designation receiving unit 15 receives a measurement item designated by the user through the operation unit 18. For example, although not shown, a list of measurement items can be displayed on the display unit 8, and one of the plurality of measurement items displayed in the list can be selected by the user through the operation unit 18. As described above, in a case where the designation of the measurement item is received, a detection measurement algorithm is set by the detection measurement algorithm setting unit 12 according to the designated measurement item.

Next, in step S2, the ultrasound diagnostic apparatus 1 starts acquiring an ultrasound image in accordance with an instruction from the user through the operation unit 18. In this case, the ultrasound probe 21 is brought into contact with the subject by the user, and the ultrasound beams are sequentially transmitted from the transmission unit 3 to the subject. The reception unit 4 of the ultrasound probe 21 receives the ultrasound echo emitted from the subject and converts it into a reception signal, and the reception signal is processed by the AD converter 5 and the image generation unit 6 to sequentially acquire ultrasound images.

Figure 4:
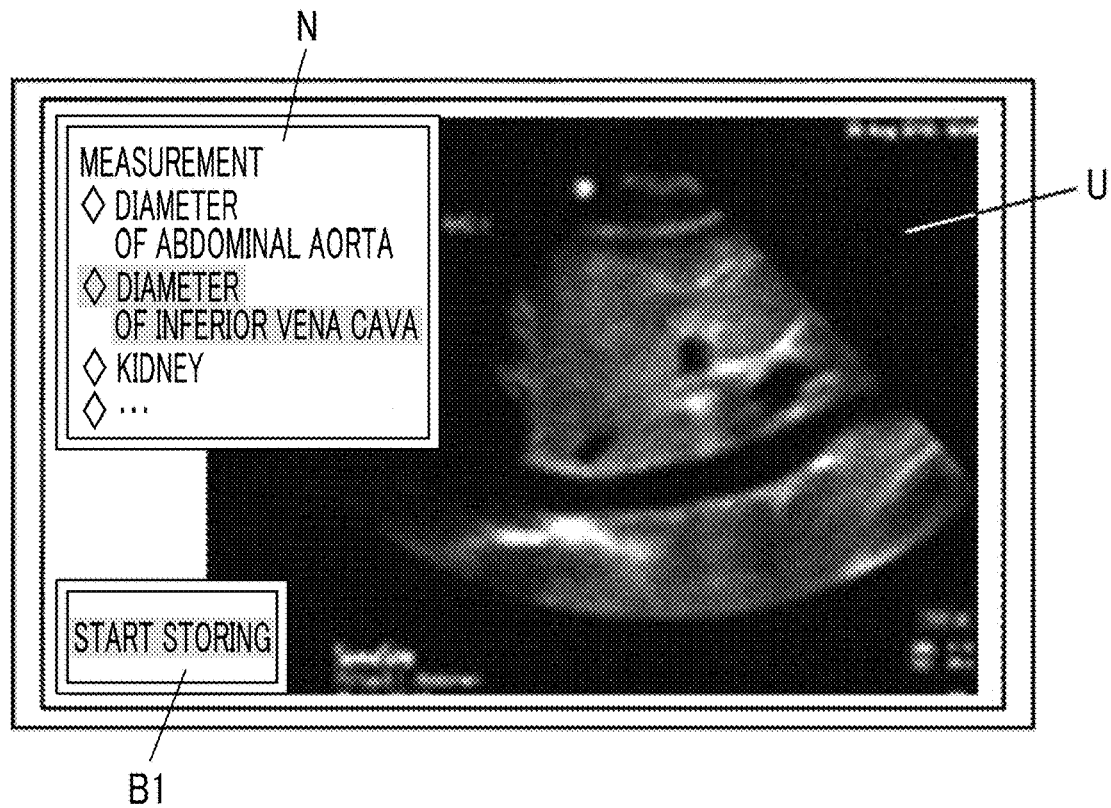
FIG. 4 is a display example on a display unit in a case where a user instructs to start a storage of an ultrasound image in the first embodiment of the present invention.

In step S3, an input for starting the storage of the acquired ultrasound image is received from the user through the operation unit 18. For example, as shown in FIG. 4, an input for starting the storage of the ultrasound images sequentially acquired in the ultrasound diagnostic apparatus 1 is received by causing a storage start button B1 to be displayed on the display unit 8 and operating the storage start button B1 by the user. In the example shown in FIG. 4, the inferior vena cava diameter is selected by the user from a plurality of measurement items displayed as a list N, and in a case where the user operates the storage start button B1, the start of the storage of an ultrasound image U representing the inferior vena cava is received.

Figure 5:
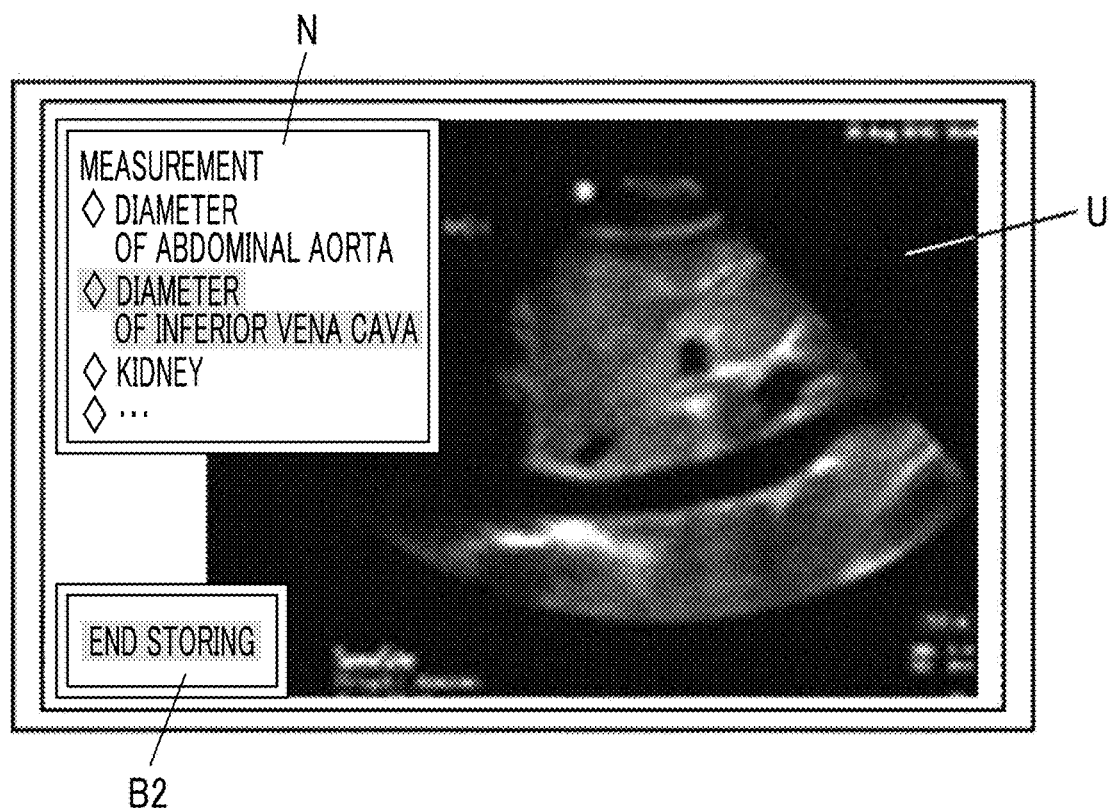
FIG. 5 is a display example on the display unit in a case where the user instructs to end the storage of the ultrasound image in the first embodiment of the present invention.

In step S4, the sequentially acquired ultrasound images are stored in the image memory 9. In this way, the ultrasound images of a plurality of frames continuous in time series are stored in the image memory 9. Further, in a case where the storage of the ultrasound images is started in step S4, for example, as shown in FIG. 5, a storage end button B2 is displayed on the display unit 8 and it is possible to receive the end of the storage of the ultrasound images by operating the storage end button B2 by the user.

In the following step S5, it is determined whether the end of the storage of the acquired ultrasound images has been received from the user through the operation unit 18. Until the end of the storage of the ultrasound images is received from the user through the operation unit 18, the storage of the ultrasound image in step S4 is continued. Further, in a case where the end of the storage of the ultrasound images is received by the user through the operation unit 18, the process proceeds to step S6, and the storage of the ultrasound images is stopped.

In the following step S7, a measurement frame to be used for a measurement among the ultrasound images of the plurality of frames stored in the image memory 9 during steps S3 to S6 is selected by the user through the operation unit 18, and the selected frame is received by the frame designation receiving unit 17 as a first measurement frame.

For example, in a case where the measurement item designated by the user through the operation unit 18 in step S1 is the inferior vena cava diameter, and the purpose is to calculate a variation rate of the inferior vena cava diameter as the final measurement value, it is desirable that a frame representing the inferior vena cava in the expiratory state or a frame representing the inferior vena cava in the inspiratory state is designated as the first measurement frame.

Figure 6:
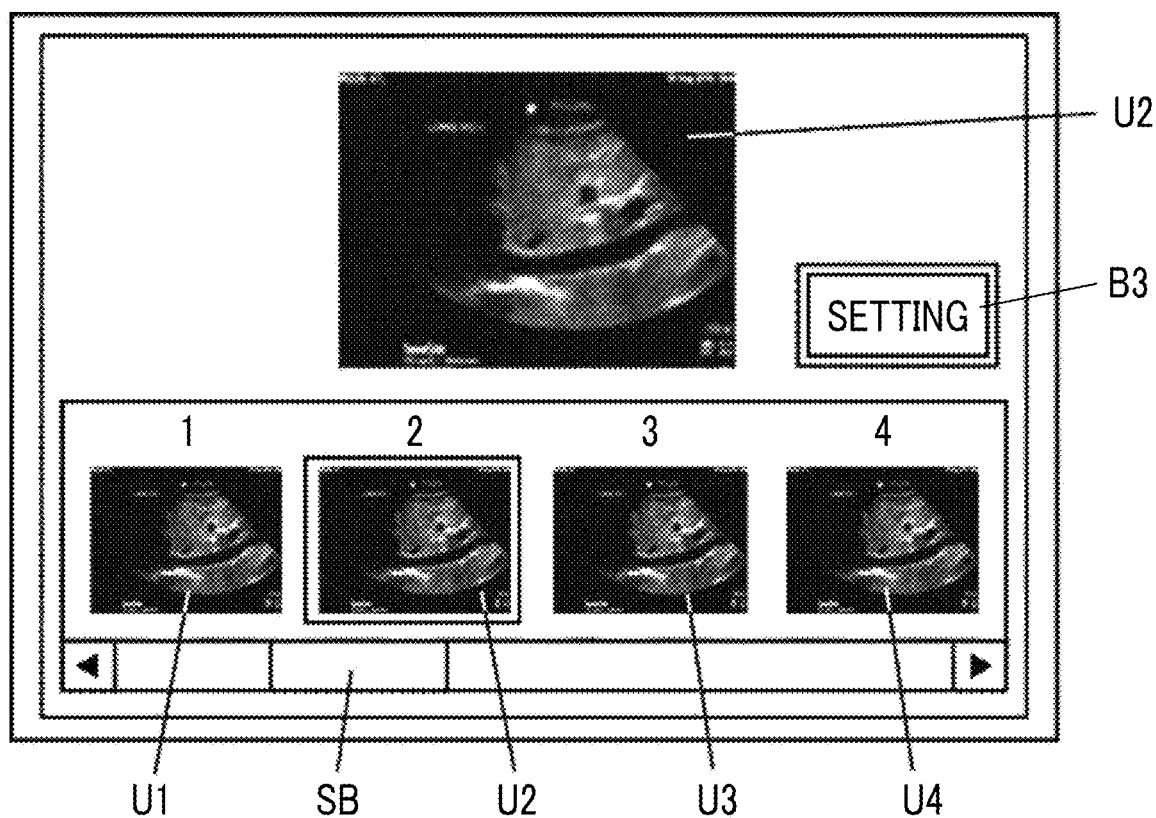
FIG. 6 is a display example on the display unit in a case where the user sets a first measurement frame in the first embodiment of the present invention.

In this case, for example, the display unit 8 displays as shown in FIG. 6. In the example shown in FIG. 6, ultrasound images U1, U2, U3, and U4 that are reduced and displayed as a list in time series, a scroll bar SB for scrolling and displaying the list of the ultrasound images, and a setting button B3 for setting the ultrasound image selected by the user through the operation unit 18 as the first measurement frame are displayed on the display unit 8. In this case, for example, one frame among the ultrasound images U1, U2, U3, and U4 displayed as a list is selected by the user through the operation unit 18. At this time, it is possible to cause the selected ultrasound image U2 to be enlarged and displayed above the ultrasound images U1, U2, U3, and U4 displayed as a list so that the user can easily grasp the selected ultrasound image.

Further, the frame designation receiving unit 17 receives the ultrasound image selected by the user through the operation unit 18 as a first measurement frame to be used for the measurement. For example, in the display example shown in FIG. 6, in a state where the ultrasound image U2 is selected by the user through the operation unit 18, the frame designation receiving unit 17 receives the ultrasound image U2 as a first measurement frame by operating the setting button B3 by the user.

Figure 7:
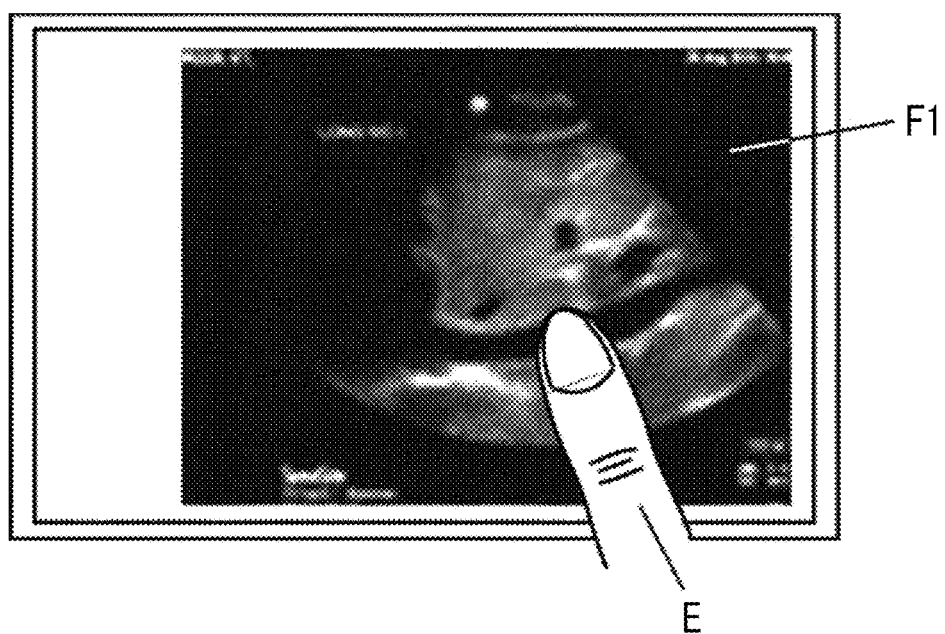
FIG. 7 is a diagram showing an example in which a user designates a position of a measurement target with respect to a first measurement frame in the first embodiment of the present invention.

In the following step S8, the measurement position designation receiving unit 16 receives a designation of the position of the measurement target on the first measurement frame from the user through the operation unit 18. In a case of designating the position of the measurement target in the first measurement frame, for example, the user may designate one approximate point in a region representing the measurement target. For example, in a case where the display unit 8 and the operation unit 18 are configured by a touch panel, as shown in FIG. 7, the user may touch one point in an area representing a measurement target with a finger E in the first measurement frame F1. In a case where the designation of the position of the measurement target is received as described above, the process proceeds to step S9.

In step S9, the measurement unit 11 performs an automatic measurement with respect to the first measurement frame based on the detection measurement algorithm set by the detection measurement algorithm setting unit 12 in step S1 and the position of the measurement target designated by the user in step S8.

First, the measurement unit 11 detects the measurement target with the recognition based on image processing, based on the detection measurement algorithm and the position of the measurement target designated by the user. For example, in a case where the measurement item designated by the user in step S1 is an inferior vena cava diameter, the measurement unit 11 sets a detection range for the first measurement frame based on the position designated by the user in step S8 and the detection measurement algorithm, and detects an image of the inferior vena cava based on the set detection range.

In this case, the measurement unit 11 determines the size of the detection range of the measurement target according to the measurement item designated by the user in step S1, and determines the position of the detection range according to the position of the measurement target designated by the user in step S8. In addition, the measurement unit 11 determines a detection order of the measurement target based on the measurement item and the position designated by the user in step S8. For example, although not shown, in a case where the measurement item is relevant to a round cross-section such as the short axis diameter of the gallbladder and the short axis diameter of the abdominal aorta, in order to reduce the time required for the detection of the measurement target, the measurement unit 11 can sequentially perform the detection of the measurement target along a spiral scanning line extending outward from the center with the position designated by the user as the center. Further, for example, in a case where the measurement item is not relevant to a round cross-section, but relevant to a cross-section extending substantially along one direction such as an inferior vena cava diameter and a common bile duct, the measurement unit 11 can search the ultrasound image including the measurement target in the horizontal direction, that is, left and right first, and then search the ultrasound image in the vertical direction, that is, up and down, thereby detecting the measurement target. Further, the search direction defined for each measurement item can be stored in the storage unit 19 or an external memory (not shown) in advance. In this case, the measurement unit 11 reads out the search direction according to the measurement item, searches the ultrasound image in the search direction corresponding to the measurement item, and then searches in a direction orthogonal to the search direction, thereby detecting the measurement target.

The measurement line to be used for the measurement of the detected measurement target is determined based on a rule determined according to the measurement item by the detection measurement algorithm. For example, in a case where the measurement item is the inferior vena cava diameter, the measurement unit 11 extracts the largest one among the line segments perpendicular to the traveling direction of the inferior vena cava and having two points on the inner wall of the inferior vena cava as end points, as a measurement line.

Finally, the measurement unit 11 calculates a measurement value based on the determined measurement line. In this case, the measurement unit 11 can store the calculated measurement value in a data memory or the like (not shown).

In a case where the automatic measurement is completed by the measurement unit 11 as described above, the process proceeds to step S10, and it is determined whether the automatic measurement is completed for all the frames stored in the image memory 9 in steps S3 to S6 by the device controller 14. Here, in a case where the device controller 14 cannot determine that the automatic measurement has been completed for all the frames stored in the image memory 9 in steps S3 to S6, the process proceeds to step S11.

Figure 8:
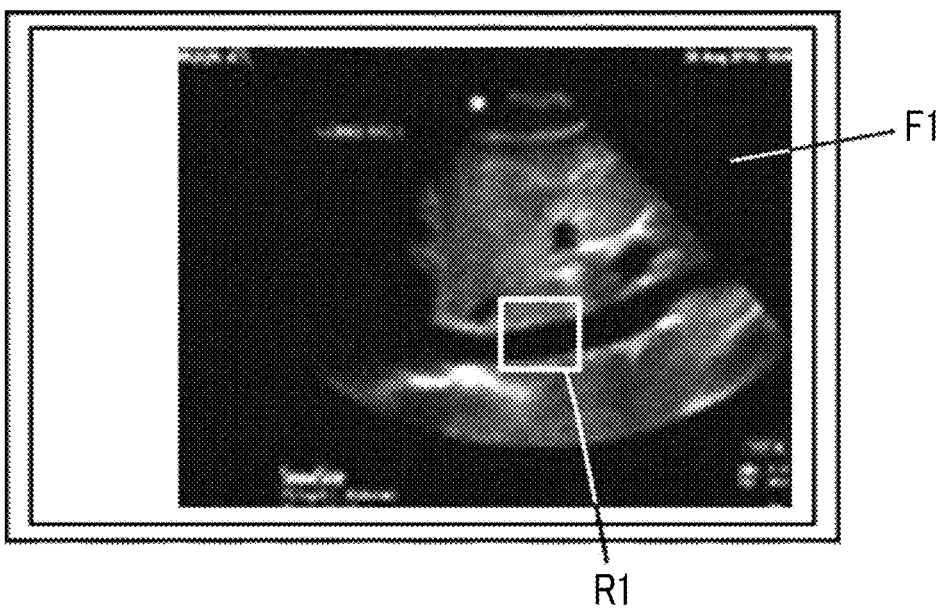
FIG. 8 is a diagram showing an example of a follow-up region of interest set in a first measurement frame in the first embodiment of the present invention.

In step S11, the measurement position setting unit 10 sets a follow-up region of interest R1 for a current frame, that is, the first measurement frame F1, as shown in FIG. 8. The follow-up region of interest R1 is a region of interest for calculating the movement amount between ultrasound images adjacent in time series. For example, the measurement position setting unit 10 can set a region around the position of the measurement target designated by the user through the operation unit 18 in step S8 as the follow-up region of interest R1. Here, the movement amount between the ultrasound images adjacent in time series is the movement distance and the movement direction between the ultrasound images adjacent in time series.

Although the shape of the follow-up region of interest R1 is not particularly limited, for the sake of explanation, it is assumed that the shape of the follow-up region of interest R1 is a square.

Figure 9:
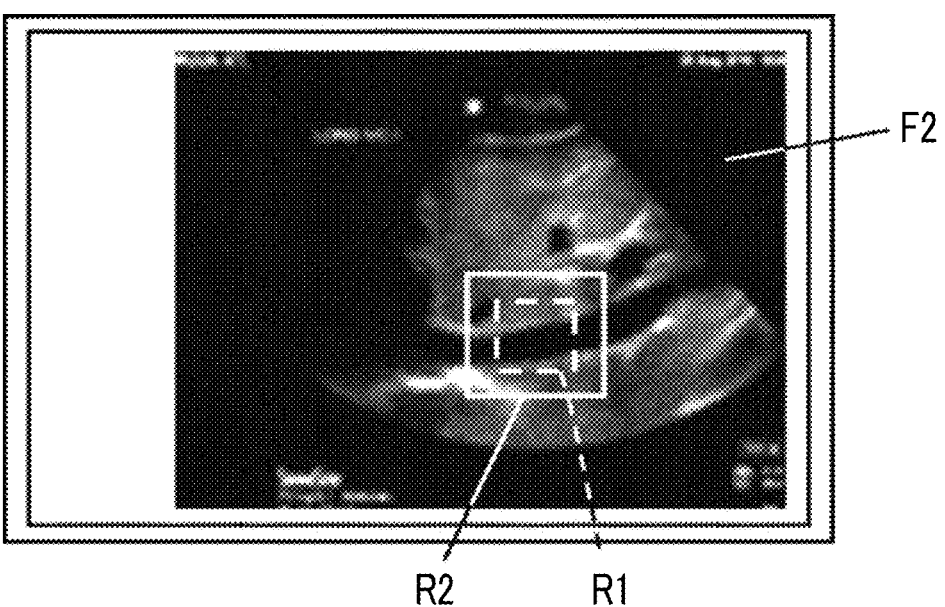
FIG. 9 is a diagram showing an example of a search region of interest and a follow-up region of interest set in a next frame in the first embodiment of the present invention.

In the following step S12, as shown in FIG. 9, the measurement position setting unit 10 sets a search region of interest R2 on the next frame, that is, the frame F2 that is adjacent to the first measurement frame in time series among the plurality of frames stored in the image memory 9. The search region of interest R2 is a region where a search for detecting the follow-up region of interest R1 is performed, and has a region larger than the follow-up region of interest R1.

Although the shape of the search region of interest R2 is not particularly limited similarly to the shape of the follow-up region of interest R1, for the sake of explanation, it is assumed that the shape of the search region of interest R2 is a square.

In the following step S13, the measurement position setting unit 10 detects the follow-up region of interest R1 within the search region of interest R2 set for the next frame F2. In this case, the measurement position setting unit 10 can analyze the search region of interest R2 by using a known technique such as so-called template matching, optical flow analysis, and feature point matching, and detect the follow-up region of interest R1 in the next frame by recognizing an image corresponding to the image in the follow-up region of interest R1 set in the first measurement frame F1.

In a case where the follow-up region of interest R1 is detected in the next frame F2, the measurement position setting unit 10 calculates the movement amount of the follow-up region of interest R1 detected in the next frame F2 with respect to the follow-up region of interest R1 set in the current frame, that is, the first measurement frame F1, that is, the movement amount of the ultrasound images between the first measurement frame F1 and the next frame F2.

In a case where the movement amount of the ultrasound images between the first measurement frame F1 and the next frame F2 is calculated in this way, the measurement position setting unit 10 sets the position of the measurement target in the next frame F2 in step S14 based on the calculated movement amount. More specifically, the measurement position setting unit 10 sets a point where the position of the measurement target in the first measurement frame F1 received by the measurement position designation receiving unit 16 is moved by the calculated movement amount as the position of the measurement target in the next frame F2.

In a case where the position of the measurement target is set in the next frame F2, the measurement unit 11 updates the next frame F2 to the current frame in step S15, and returns to step S9. In step S9, the automatic measurement is performed on the frame F2 updated as the current frame in step S15. In this case, the measurement unit 11 can store the calculated measurement value in a data memory or the like (not shown).

In the following step S10, the device controller 14 determines whether the automatic measurement has been completed for all the frames stored in the image memory 9, and in a case where the device controller 14 cannot determine that the automatic measurement has been completed for all the frames, the process proceeds to step S11 and the follow-up region of interest R1 is set in the current frame F2. In step S12, the search region of interest R2 and the follow-up region of interest R1 are set for the next frame that is not the first measurement frame F1 and that is adjacent to the current frame F2 in time series. Then, the movement amount of the follow-up region of interest R1 between the current frame F2 and the next frame is calculated in step S13, and in a case where the position of the measurement target with respect to the next frame is set in step S14, the frame is updated in step S15 and the process returns to step S9.

In this way, the position of the measurement target in a frame other than the first measurement frame among the plurality of frames stored in an image memory 9 is set by the measurement position setting unit 10, and steps S9 to S15 are repeated until the automatic measurement is performed by the measurement unit 11 for each frame. As a result, in a case where the device controller 14 determines that the automatic measurement has been completed for all the frames stored in the image memory 9 in step S10, the process proceeds to step S16.

Figure 10:
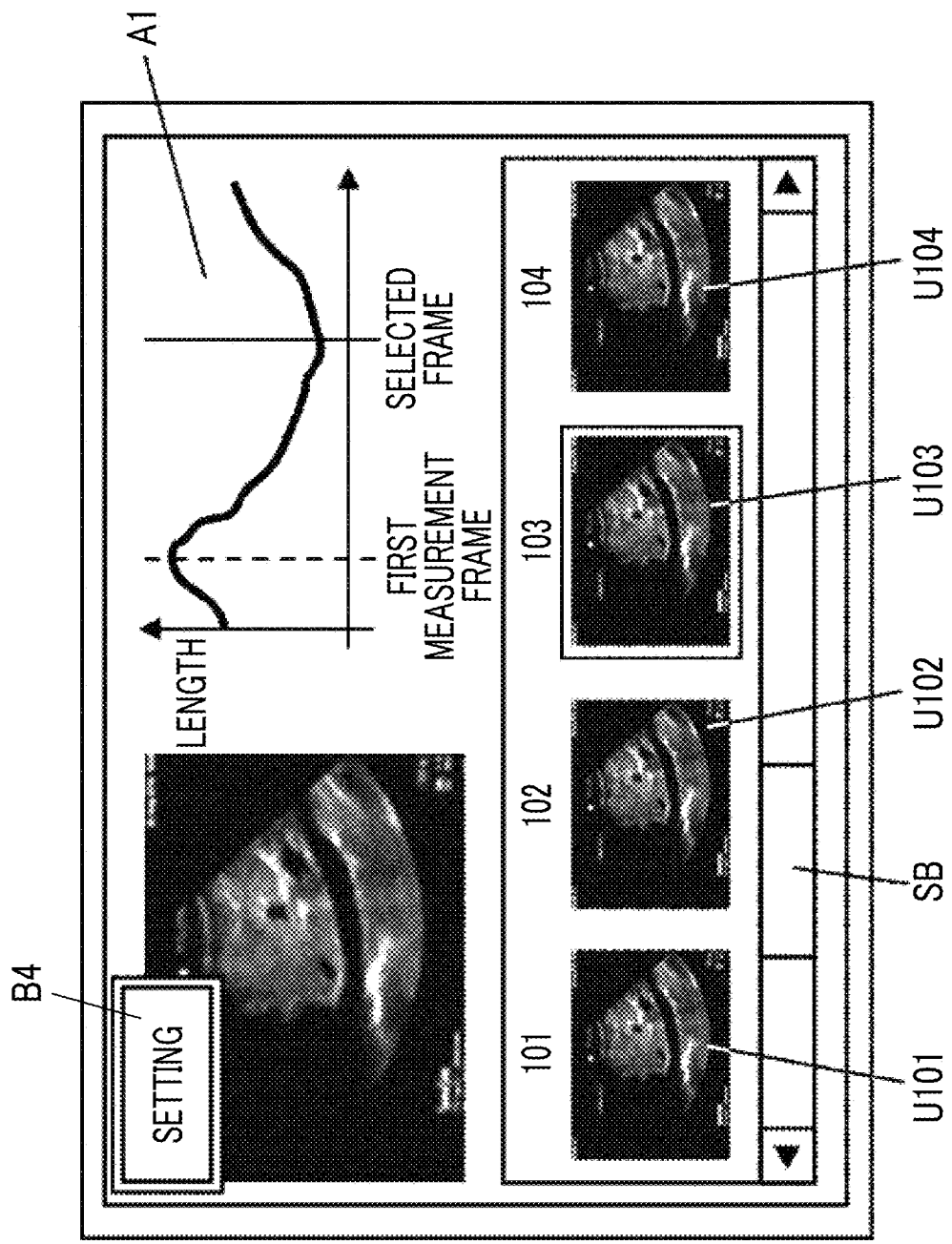
FIG. 10 is a diagram showing a display example on the display unit in a case where the user sets a second measurement frame in the first embodiment of the present invention.

In step S16, the measurement unit 11 displays the measurement values on the display unit 8 for all the frames stored in the image memory 9 obtained by repeating steps S9 to S15, as shown in FIG. 10. In the example shown in FIG. 10, a plurality of measurement values are displayed on the display unit 8 as a measurement value graph A1 in which the measurement values, that is, the lengths of the inferior vena cava are plotted in the order of the frames corresponding to the measurement values.

In the following step S17, one frame is selected from the all frames stored in the image memory 9 by the user through the operation unit 18, and the frame selected by the user is received as a second measurement frame to be used for calculating the final measurement value by the frame designation receiving unit 17.

Here, for example, in a case where the inferior vena cava diameter is selected as the measurement item by the user through the operation unit 18 in step S1, the variation rate of the inferior vena cava diameter is often calculated as the final measurement value. In that case, in a case where the user selects one frame from the plurality of frames, for example, in a case where a frame representing the inferior vena cava in the expiratory state, that is, a frame with the maximum diameter of the inferior vena cava is selected as the first measurement frame F1, the user desirably selects a frame representing the inferior vena cava in the inspiratory state, that is a frame with the minimum diameter of the inferior vena cava as the second measurement frame. Further, for example, in a case where the frame representing the inferior vena cava in the inspiratory state is selected as the first measurement frame F1, the user desirably selects a frame representing the inferior vena cava in the expiratory state as the second measurement frame.

In the example shown in FIG. 10, among the ultrasound images U101, U102, U103, and U104 displayed as a list, the ultrasound image U103 having the minimum measurement value is selected as the second measurement frame by the user, and the ultrasound image U103 selected by the user is enlarged and displayed above the ultrasound images U101, U102, U103, and U104 displayed as a list. Further, in the example shown in FIG. 10, the setting button B4 is displayed so as to be superimposed on the ultrasound image U103 displayed in an enlarged manner, and in a state where the ultrasound image U103 is selected by the user, the frame designation receiving unit 17 receives the ultrasound image U103 as a second measurement frame by the operation of the setting button B4 by the user.

In a case where the second measurement frame is received by the frame designation receiving unit 17 in this way, in step S18, the final measurement value calculation unit 13 calculates a final measurement value based on the measurement value in the first measurement frame F1 and the measurement value in the second measurement frame. For example, in a case where the inferior vena cava diameter is designated as the measurement item by the user through the operation unit 18 in step S1, the final measurement value calculation unit 13 can calculate a value obtained by dividing a measurement value having a smaller value by a measurement value having a larger value among the measurement value in the first measurement frame and the measurement value in the second measurement frame as a final measurement value in order to calculate the variation rate of the inferior vena cava diameter.

In the following step S19, the final measurement value calculation unit 13 displays the calculated final measurement value on the display unit 8. In this way, the operation of the ultrasound diagnostic apparatus 1 according to the first embodiment ends.

As described above, according to the ultrasound diagnostic apparatus 1 of the first embodiment, since an approximate position of the measurement target is set for a frame other than the first measurement frame F1, and the measurement target is detected for all the frames stored in the image memory 9 and the measurement is automatically performed based on the detection measurement algorithm by simply selecting the first measurement frame F1 from the plurality of frames stored in the image memory 9 and designating the approximate position of the measurement target with respect to the first measurement frame F1 by the user, it is not necessary for the user to perform the measurement operation for each of the plurality of frames. Thereby, the user may select the second measurement frame by referring to the measurement value which is already automatically calculated, and can easily obtain the final measurement value.

In addition, since the measurement unit 11 displays all the calculated measurement values on the display unit 8 as the measurement value graph A1, it is easy for the user to visually grasp the measurement values, and the burden of selecting the second measurement frame can be reduced.

Figure 11:
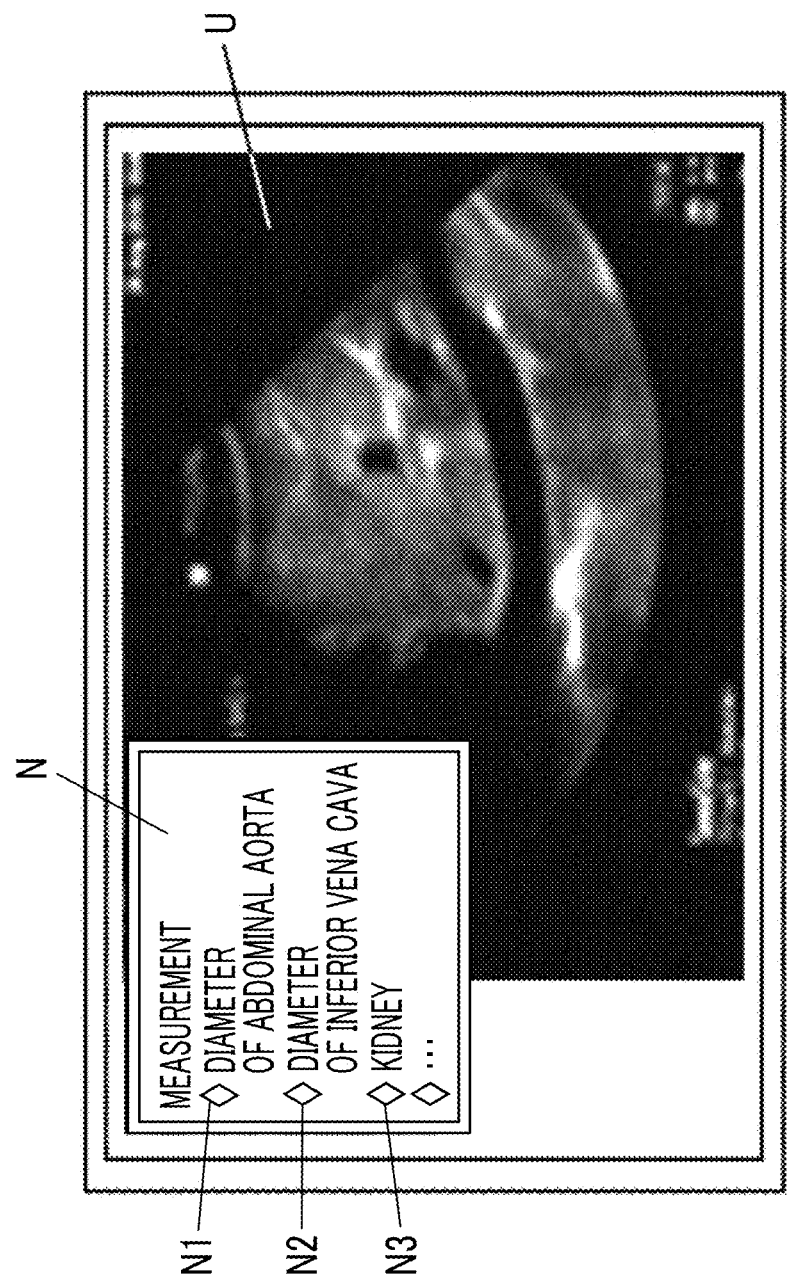
FIG. 11 is a diagram showing a display example on a display unit in a case where a user designates a measurement item in a modification of the first embodiment of the present invention.

In the first embodiment, the acquisition of the ultrasound image is started in step S2 after the measurement item designated by the user through the operation unit 18 is received in step S1, but the designation of the measurement item can be received after the acquisition of the ultrasound image is started. For example, as shown in FIG. 11, in a case where the acquisition of the ultrasound image is started, the ultrasound image U is displayed on the display unit 8 and the list N of measurement items can be superimposed and displayed on the ultrasound image U. In this example, the abdominal aorta diameter, the inferior vena cava diameter, and the kidney are respectively displayed as the measurement items N1 to N3 in the list N, and the user can designate the measurement item by selecting one of the plurality of measurement items included in the list N through the operation unit 18.

Further, in step S11, the measurement position setting unit 10 sets the follow-up region of interest R1 such that the position of the measurement target designated by the user through the operation unit 18 in step S8 is the center of the follow-up region of interest R1 with respect to the first measurement frame F1, but, in a case where the movement amount between the frames adjacent in time series can be calculated and the measurement value can be calculated with high accuracy in the frame adjacent in time series with respect to the first measurement frame F1, the method of setting the follow-up region of interest R1 is not limited to this.

For example, in a case where the measurement line set for the measurement target by the measurement unit 11 is a line segment for calculating a distance, the measurement position setting unit 10 can set the follow-up region of interest R1 for the first measurement frame F1 so that the center of this line segment is the center of the follow-up region of interest R1. Further, for example, in a case where the measurement line set for the measurement target by the measurement unit 11 is a closed curve for calculating the area, the measurement position setting unit 10 can set the follow-up region of interest R1 for the first measurement frame F1 so that the center of gravity of the closed curve is the center of the follow-up region of interest R1.

Also, the size of the follow-up region of interest R1 set for the current frame in step S11 can be determined based on the measurement line set by the measurement unit 11 for the current frame. For example, in a case where the measurement line is a line segment and the follow-up region of interest R1 is a square, the measurement position setting unit 10 can set the follow-up region of interest R1 by setting the length of one side of the follow-up region of interest R1 to a value obtained by multiplying the linear measurement line by a predetermined ratio. Further, for example, in a case where the measurement line is a closed curve, the measurement position setting unit 10 can set the follow-up region of interest R1 so that the area of the region surrounded by the follow-up region of interest R1 is a value obtained by multiplying the area of the region surrounded by the closed curve by a predetermined ratio.

Further, the size of the follow-up region of interest R1 can be fixed to a predetermined size or can be set by the user through the operation unit 18.

Further, the size of the search region of interest R2 set for the next frame in step S12 can be set based on the size of the follow-up region of interest R1 set for the current frame in step S11. For example, in a case where both the follow-up region of interest R1 and the search region of interest R2 are square, the measurement position setting unit 10 can set the search region of interest R2 so that the length of one side of the search region of interest R2 is a value obtained by adding a determined length to the length of one side of the follow-up region of interest R1.

Further, the size of the search region of interest R2 can be fixed to a predetermined size or can be set by the user through the operation unit 18.

Although not shown, the ultrasound diagnostic apparatus 1 may further comprise a final measurement value determination unit that determines the final measurement value calculated by the final measurement value calculation unit 13 in step S18. For example, in a case where the final measurement value exceeds a predetermined value, the final measurement value determination unit can display a message indicating that fact on the display unit 8 through the display controller 7. Further, the final measurement value determination unit can also issue a message indicating that the final measurement value has exceeded a predetermined value as a voice. Thereby, since the user can be urged to pay attention to the value of the final measurement value, the user can perform a more accurate diagnosis.

Further, in the first embodiment of the present invention, although the measurement of the measurement target is performed by using the ultrasound image, the measurement can be performed on the acoustic wave image other than the ultrasound image. For example, in a case where the ultrasound diagnostic apparatus 1 comprises a device that emits and receives laser light in addition to the ultrasound probe 21, the measurement target can also be measured on a photoacoustic wave image and a composite image in which an ultrasound image and a photoacoustic wave image are superimposed.

Second Embodiment

In the ultrasound diagnostic apparatus 1 according to the first embodiment, although the second measurement frame is set by causing the user to refer to the measurement values in the plurality of frames calculated by the measurement unit 11, an ultrasound diagnostic apparatus 1A according to a second embodiment can further calculate the reliabilities with respect to the measurement values in the plurality of frames and cause the user to further refer to the calculated reliabilities.

Figure 12:
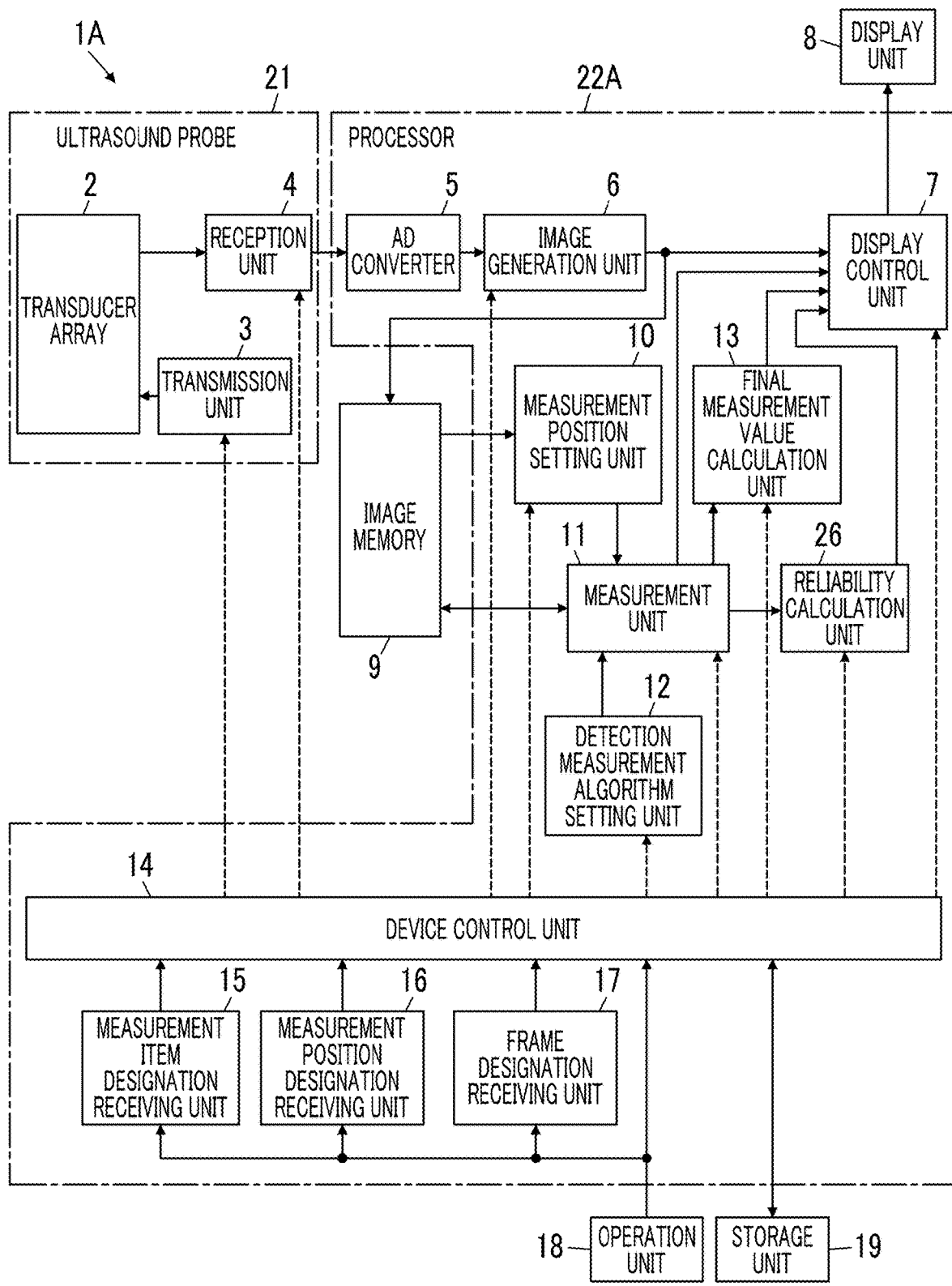
FIG. 12 is a block diagram showing a configuration of an ultrasound diagnostic apparatus according to a second embodiment of the present invention.

FIG. 12 shows a configuration of the ultrasound diagnostic apparatus 1A according to a second embodiment. In the ultrasound diagnostic apparatus 1A according to the second embodiment, a reliability calculation unit 26 is connected to the measurement unit 11, and the display controller 7 and the device controller 14 are connected to the reliability calculation unit 26, respectively. Further, a processor 22A is configured by the AD converter 5, the image generation unit 6, the display controller 7, the measurement position setting unit 10, the measurement unit 11, the detection measurement algorithm setting unit 12, the final measurement value calculation unit 13, the device controller 14, the measurement item designation receiving unit 15, the measurement position designation receiving unit 16, the frame designation receiving unit 17, and the reliability calculation unit 26.

Here, the ultrasound diagnostic apparatus 1A of the second embodiment has the same configuration as that of the ultrasound diagnostic apparatus 1 of the first embodiment shown in FIG. 1, except that the ultrasound diagnostic apparatus 1A comprises the reliability calculation unit 26.

The reliability calculation unit 26 of the processor 22A calculates the reliabilities of the measurement values calculated by the measurement unit 11 with respect to the ultrasound images of the plurality of frames stored in the image memory 9, and displays the calculated reliabilities on the display unit 8. Here, the reliability of the measurement value is an index indicating the certainty of the measurement value, and the measurement value having higher reliability can be determined to be more accurate. For example, in a case where the measurement line at the time of calculating the measurement value is a line segment for measuring the length between two points, the reliability calculation unit 26 can calculate the reliability of the measurement value based on the edge strength of the ultrasound image at the end points of the line segment. The edge strength indicates the contour likeness in the target part on the image, and the reliability based on the edge strength of the image at the target point can be calculated by image recognition using, for example, the contrast between the target point and surrounding points.

Further, in a case of calculating the reliability with respect to the measurement value, the reliability calculation unit 26 can store the calculated reliability in a data memory (not shown) or the like.

Next, the operation of the ultrasound diagnostic apparatus 1A according to the second embodiment will be described with reference to the flowchart shown in FIG. 13.

Figure 3:
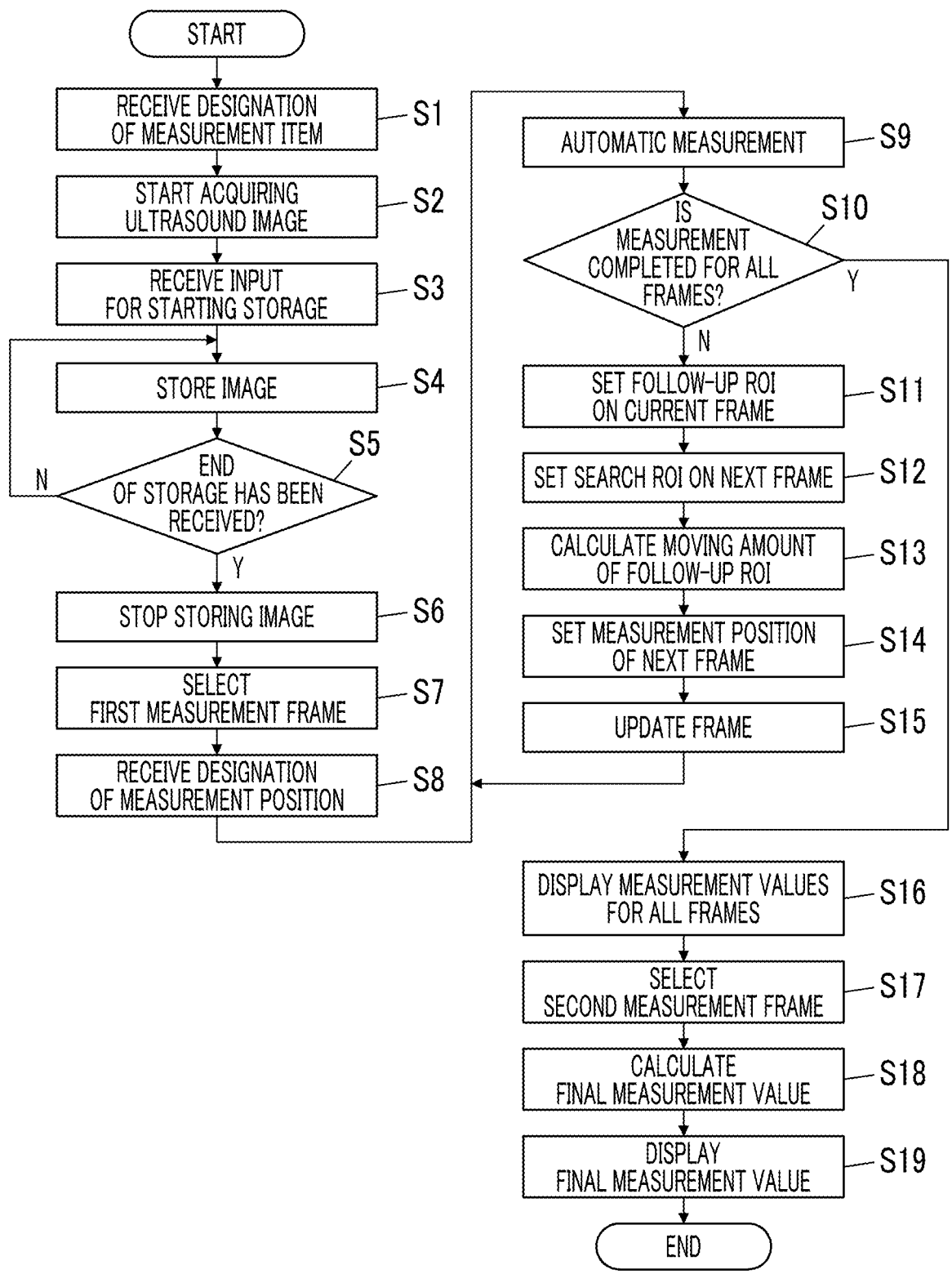
FIG. 3 is a flowchart showing an operation of the ultrasound diagnostic apparatus according to the first embodiment of the present invention.
Figure 13:
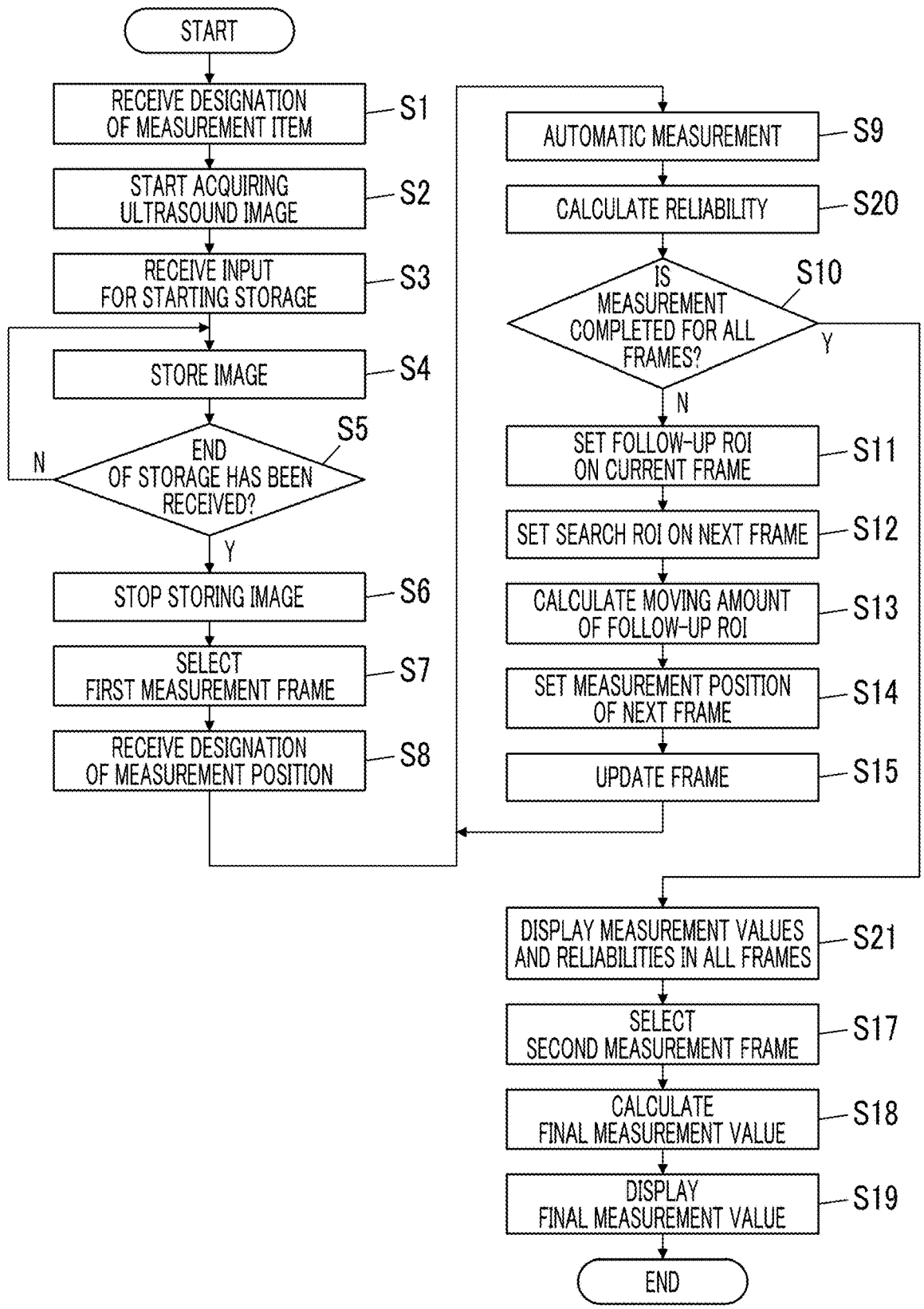
FIG. 13 is a flowchart showing an operation of an ultrasound diagnostic apparatus in the second embodiment of the present invention.

Steps S1 to S9 in the flowchart shown in FIG. 13 are the same as steps S1 to S9 of the first embodiment shown in FIG. 3. That is, first, in a case where the measurement item designated by the user through the operation unit 18 is received, acquisition of the ultrasound image is started. Next, the ultrasound image acquired from the time when the instruction to start storing the ultrasound image is given by the user through the operation unit 18 to the time when the instruction to end storing the ultrasound image is given is stored in the image memory 9. In a case where the ultrasound images of the plurality of frames are stored in the image memory 9, one frame among the stored plurality of frames is selected as the first measurement frame F1 by the user through the operation unit 18. In a case where the user designates an approximate position of the measurement target with respect to the first measurement frame F1, the automatic measurement of the measurement target is performed on the first measurement frame F1 by the measurement unit 11.

In a case where the automatic measurement is performed on the first measurement frame F1 in step S9, the process proceeds to step S20. In step S20, the reliability calculation unit 26 calculates the reliability with respect to the measurement value calculated in step S9. For example, in a case where the measurement line used for the measurement in step S9 is a line segment for measuring the length, the reliability calculation unit 26 calculates the reliability of the measurement value based on the edge strength of the ultrasound image at the end points of the measurement line.

In the following step S10, the device controller 14 determines whether the calculation of the measurement values and the reliabilities has been completed for all the frames stored in the image memory 9 in steps S3 to S6. Here, in a case where the device controller 14 cannot determine that the calculation of the measurement values and the reliabilities has been completed for all the frames stored in the image memory 9 in steps S3 to S6, the process proceeds to step S11.

Steps S11 to S15 are the same as steps S11 to S15 in the first embodiment shown in FIG. 3. That is, the measurement position setting unit 10 sets the follow-up region of interest R1 for the first measurement frame F1, which is the current frame, and sets the search region of interest R2 for the next frame F2. Next, the measurement position setting unit 10 detects the follow-up region of interest R1 in the next frame F2 by performing the image analysis or the like on the search region of interest R2 in the next frame F2, and calculates the movement amount of the follow-up region of interest R1. The position of the measurement target is set for the next frame F2 based on the calculated movement amount of the follow-up region of interest R1, and the frame is updated.

In a case where the frame is updated in step S15, that is, in a case where the frame F2 is updated as the current frame, the process returns to step S9, and the automatic measurement on the frame F2 is performed by the measurement unit 11. In a case where the reliability with respect to the measurement value in the frame F2 is calculated by the reliability calculation unit 26 in step S20, the process proceeds to step S10.

As described above, in a case where it is determined in step S10 that the calculation of the measurement values and the reliabilities in all the frames stored in the image memory 9 in steps S3 to S6 is completed as a result of repeating the processes of steps S9, S20 and steps S10 to S15, the process proceeds to step S21.

Figure 14:
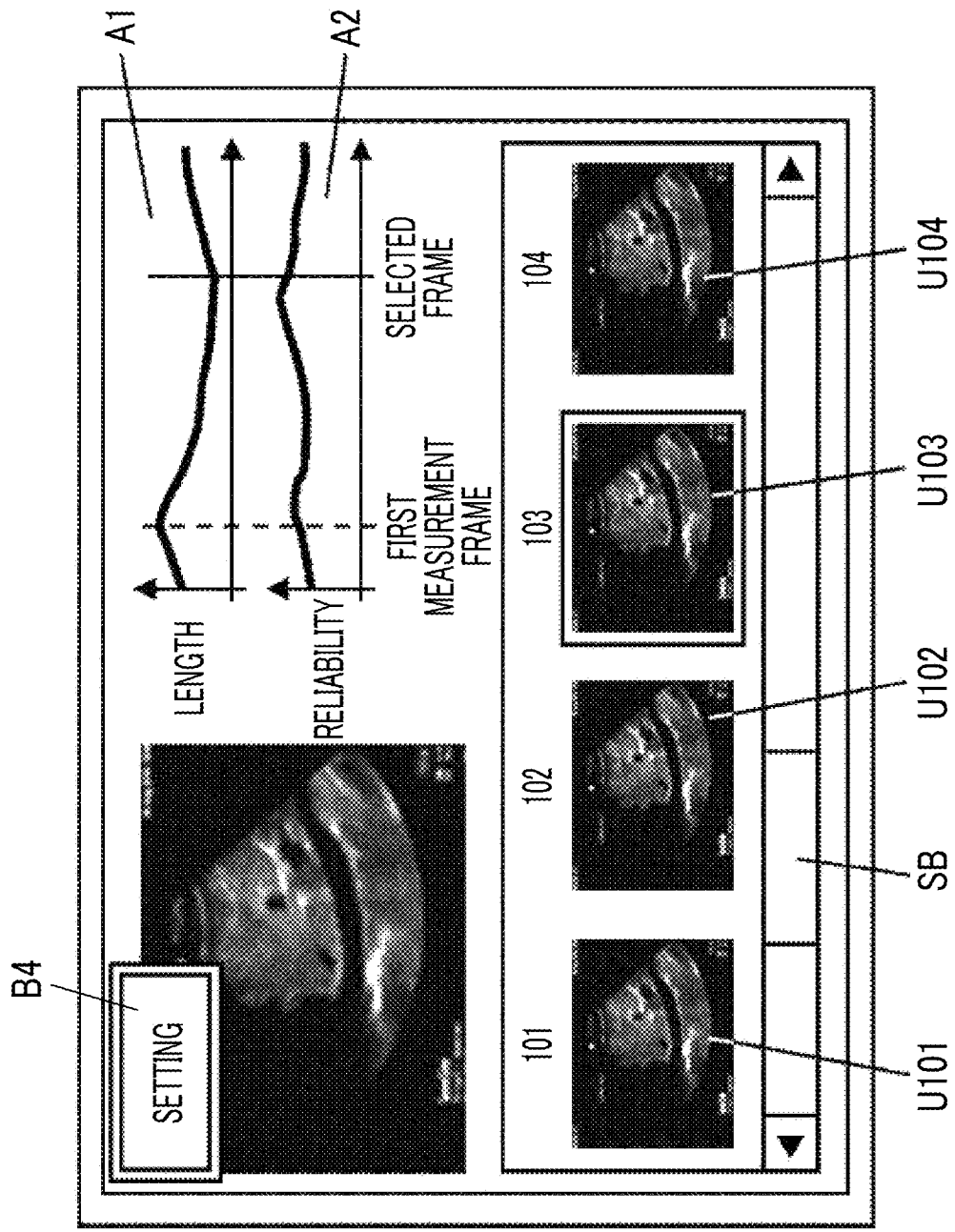
FIG. 14 is a diagram showing a display example on a display unit in a case where a user sets a second measurement frame in the second embodiment of the present invention.

In step S21, the measurement unit 11 and the reliability calculation unit 26 display the measurement values and the reliabilities in all the frames stored in the image memory 9 in steps S3 to S6 on the display unit 8, as shown in FIG. 14. In the example shown in FIG. 14, a measurement value graph A1 in which the measurement values, that is, the lengths of the diameters of the inferior vena cava are plotted in the order of the frames corresponding to the measurement values and a reliability graph A2 in which the reliabilities with respect to each measurement value are plotted in the order of the frames corresponding to the measurement values are displayed on the display unit 8.

In the following step S17, one frame is selected from all the frames stored in the image memory 9 in steps S3 to S6 by the user through the operation unit 18, and the frame selected by the user is received by the frame designation receiving unit 17 as the second measurement frame to be used for calculating the final measurement value. In this case, in the ultrasound diagnostic apparatus 1A of the second embodiment, as shown in FIG. 14, in addition to the plurality of measurement values, the reliabilities with respect to these measurement values are displayed on the display unit 8, so that the user can select the second measurement frame by referring to the reliability in addition to the measurement value. Since the reliability is an index indicating the certainty of the measurement value, for example, the user can select a frame having a measurement value of which the reliability with respect to the measurement value is equal to or more than a certain value as the second measurement frame.

In the example shown in FIG. 14, the ultrasound image U103 is selected by the user from the ultrasound images U101, U102, U103, and U104 displayed as a list. In a case where the setting button B4 is operated by the user through the operation unit 18 in this state, the ultrasound image U103 selected by the user is set as the second measurement frame.

Subsequent steps S18 and S19 are the same as steps S18 and S19 in the first embodiment shown in FIG. 3. That is, the final measurement value calculation unit 13 calculates the final measurement value from the measurement value in the first measurement frame and the measurement value in the second measurement frame, and displays the calculated final measurement value on the display unit 8. In this way, the operation of the ultrasound diagnostic apparatus 1A according to the second embodiment ends.

As described above, according to the ultrasound diagnostic apparatus 1A of the second embodiment, since the reliabilities are automatically calculated with respect to the measurement values in all the frames stored in the image memory 9 to be displayed on the display unit 8 together with the measurement values by performing a designation of the measurement position with respect to the first measurement frame by the user, the user can easily select the second measurement frame having a value appropriate for the calculation of the final measured value.

In the second embodiment, although a case where the reliability calculation unit 26 calculates the reliability of the measurement value based on the edge strength of the ultrasound image at the end points of the measurement line in a case where the measurement line used for calculating the measurement value is a line segment for measuring the length between two points has been exemplified, but the method of calculating the reliability is not limited to this. For example, in a case where the measurement line used for calculating the measurement value is a line segment, the reliability calculation unit 26 can calculate the reliability of the measurement value based on the angle between the edge in the ultrasound image and the measurement line. In this case, the reliability can be calculated so that, for example, the value increases as the angle between the edge in the ultrasound image and the measurement line is closer to a right angle.

Further, for example, in a case where the measurement line used for calculating the measurement value is a closed curve for calculating the area, the reliability can be calculated based on the circularity of the contour of the measurement line, the average value of the edge strengths of the ultrasound image on the contour of the measurement line, and the like. For example, in a case where the measurement item is relevant to a measurement target having a substantially circular shape, such as the short axis diameter of the gallbladder and the short axis diameter of the abdominal aorta, the measurement unit 11 determines that the contour of the measurement target can be extracted more accurately as the circularity of the measurement line is larger, and can calculate the reliability higher. In addition, for example, the measurement unit 11 determines that the contour of the measurement target can be extracted more accurately as the average value of the edge strengths of the ultrasound image on the contour of the measurement line is larger, and the reliability can be calculated higher.

Third Embodiment

In the ultrasound diagnostic apparatus 1 according to the first embodiment and the ultrasound diagnostic apparatus 1A according to the second embodiment, the user selects the second measurement frame to be used for calculating the final measurement value, but an ultrasound diagnostic apparatus 1B according to a third embodiment can automatically set the second measurement frame.

Figure 15:
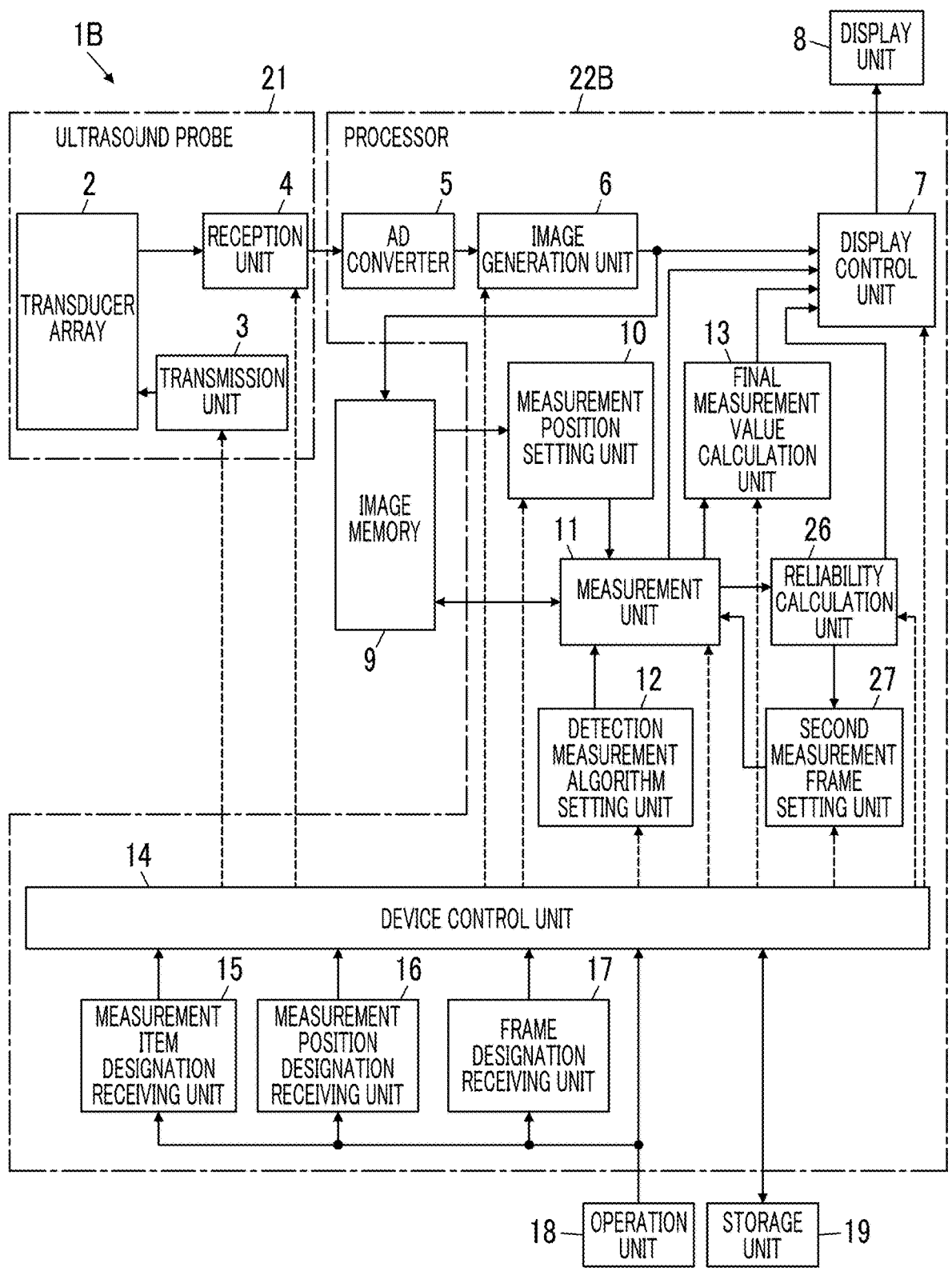
FIG. 15 is a block diagram showing a configuration of an ultrasound diagnostic apparatus according to a third embodiment of the present invention.

FIG. 15 shows a configuration of an ultrasound diagnostic apparatus 1B according to a third embodiment. In the ultrasound diagnostic apparatus 1B of the third embodiment, a second measurement frame setting unit 27 is connected to the reliability calculation unit 26, and the measurement unit 11 and the device controller 14 are respectively connected to the second measurement frame setting unit 27. In addition, a processor 22B is configured by the AD converter 5, the image generation unit 6, the display controller 7, the measurement position setting unit 10, the measurement unit 11, the detection measurement algorithm setting unit 12, the device controller 14, the measurement item designation receiving unit 15, the measurement position designation receiving unit 16, the frame designation receiving unit 17, the reliability calculation unit 26, and the second measurement frame setting unit 27.

Here, the ultrasound diagnostic apparatus 1B according to the third embodiment has the same configuration as that of the ultrasound diagnostic apparatus 1A according to the second embodiment shown in FIG. 12 except that the ultrasound diagnostic apparatus 1B comprises a second measurement frame setting unit 27.

The second measurement frame setting unit 27 of the processor 22B automatically sets a second measurement frame from a plurality of frames stored in the image memory 9 based on the measurement value calculated by the measurement unit 11 or both the measurement value calculated by the measurement unit 11 and the reliability calculated by the reliability calculation unit 26.

Figure 16:
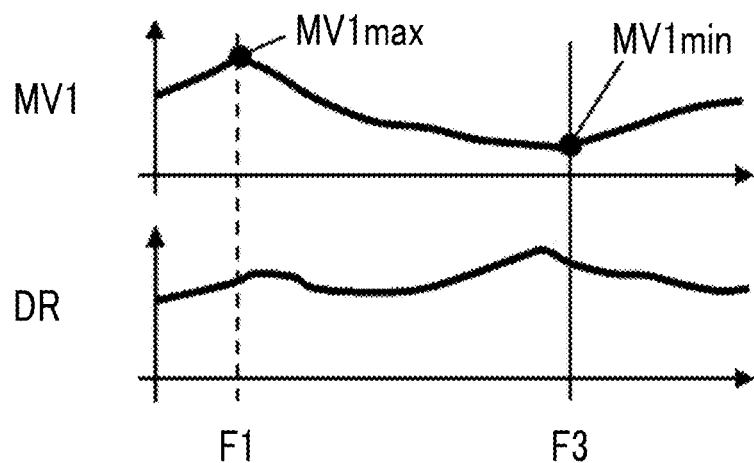
FIG. 16 is a conceptual diagram showing a state where a second measurement frame is set in the third embodiment of the present invention.

For example, as shown in FIG. 16, in a case where a measurement value MV1 in the first measurement frame F1 is the maximum value MV1max, the second measurement frame setting unit 27 can set the frame having the minimum value MV1min among the plurality of measurement values MV1 in the plurality of frames as the second measurement frame F3.

Also, for example, although not shown, in a case where the measurement value MV1 in the first measurement frame F1 is the minimum value MV1min, the second measurement frame setting unit 27 can set the frame having the maximum value MV1max among the plurality of measurement values MV1 in the plurality of frames as the second measurement frame F3.

Figure 17:
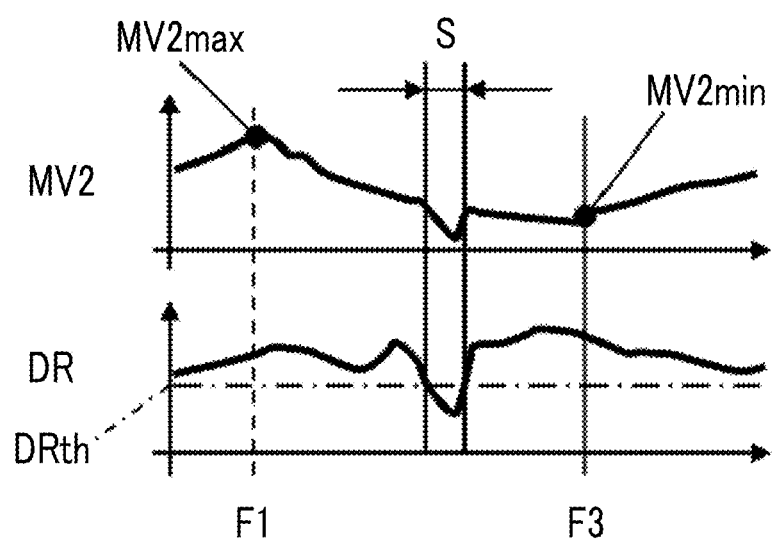
FIG. 17 is a conceptual diagram showing another state where the second measurement frame is set in the third embodiment of the present invention.

Further, the second measurement frame setting unit 27 can also set the second measurement frame F3 with reference to a reliability DR. For example, as shown in FIG. 17, in a case where a measurement value MV2 in the first measurement frame F1 is a maximum value MV2max, the second measurement frame setting unit 27 can set a frame having a minimum value MV2min among the plurality of measurement values MV2 in the plurality of frames as the second measurement frame F3 after excluding the frames included in a range S where the reliability DR is equal to or less than a certain value DRth from the targets to be set as the second measurement frame F3.

Although not shown, the second measurement frame setting unit 27 can set the frame having the maximum value MV2max among the plurality of measurement values MV2 in the plurality of frames as the second measurement frame F3 after excluding the frames included in the range S in which the reliability DR is equal to or less than the certain value DRth from the targets to be set as the second measurement frame, similarly in a case where the measurement value MV2 in the first measurement frame F1 is the minimum value MV2min.

As described above, according to the ultrasound diagnostic apparatus 1B of the third embodiment, since the second measurement frame F3 is automatically set based on the measurement value calculated by the measurement unit 11 and the reliability calculated by the reliability calculation unit 26, there is no need for the user to select the second measurement frame F3 with reference to the ultrasound image, the measurement value, and the reliability, thereby the final measurement value can be calculated while further reducing the burden on the user.

In addition, since the second measurement frame F3 can be automatically set with reference to the measurement value V1 having higher reliability by excluding a frame in a range where the reliability is equal to or less than a certain value from a target to be selected as the second measurement frame F3, the accuracy in calculating the final measurement value can be improved.

Fourth Embodiment

In the first to third embodiments, the measurement values are calculated for all the frames stored in the image memory 9, but an ultrasound diagnostic apparatus 1C according to a fourth embodiment can limit the frames in which the measurement values are calculated.

Figure 18:
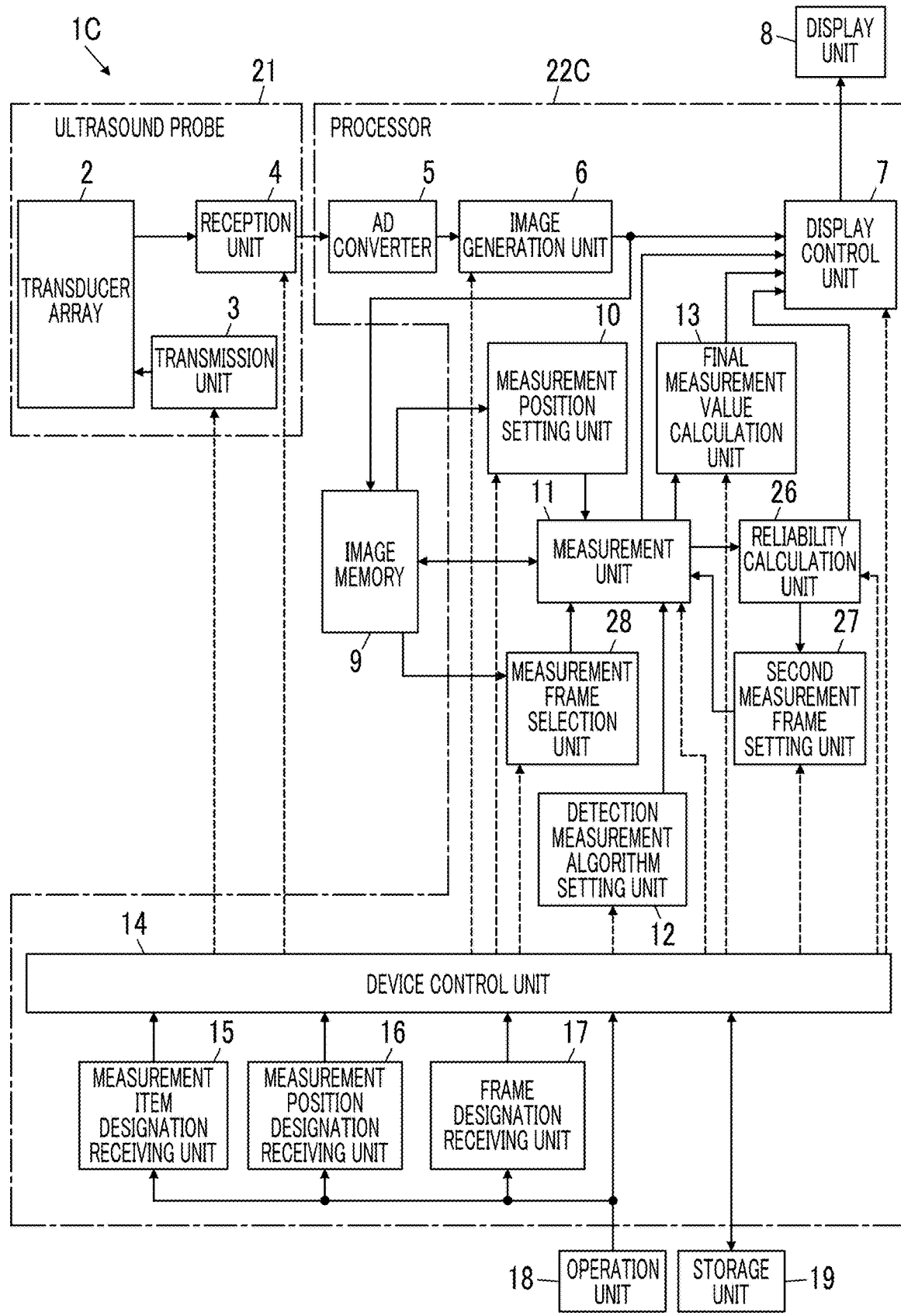
FIG. 18 is a block diagram showing a configuration of an ultrasound diagnostic apparatus according to a fourth embodiment of the present invention.

FIG. 18 shows a configuration of an ultrasound diagnostic apparatus 1C according to a fourth embodiment. In the ultrasound diagnostic apparatus 1C, a measurement frame selection unit 28 is connected to the image memory 9, and the measurement unit 11 and the device controller 14 are respectively connected to the measurement frame selection unit 28.

In addition, a processor 22C is configured by the AD converter 5, the image generation unit 6, the display controller 7, the measurement position setting unit 10, the measurement unit 11, the detection measurement algorithm setting unit 12, the final measurement value calculation unit 13, the device controller 14, the measurement item designation receiving unit 15, the measurement position designation receiving unit 16, the frame designation receiving unit 17, the reliability calculation unit 26, the second measurement frame setting unit 27, and the measurement frame selection unit 28.

Here, the ultrasound diagnostic apparatus 1C according to the fourth embodiment has the same configuration as that of the ultrasound diagnostic apparatus 1B according to the third embodiment shown in FIG. 15 except that the ultrasound diagnostic apparatus 1C comprises the measurement frame selection unit 28.

The measurement frame selection unit 28 of the processor 22C selects a part of frames from among the plurality of frames stored in the image memory 9 for detecting and measuring the measurement target by the measurement unit 11.

Figure 19:
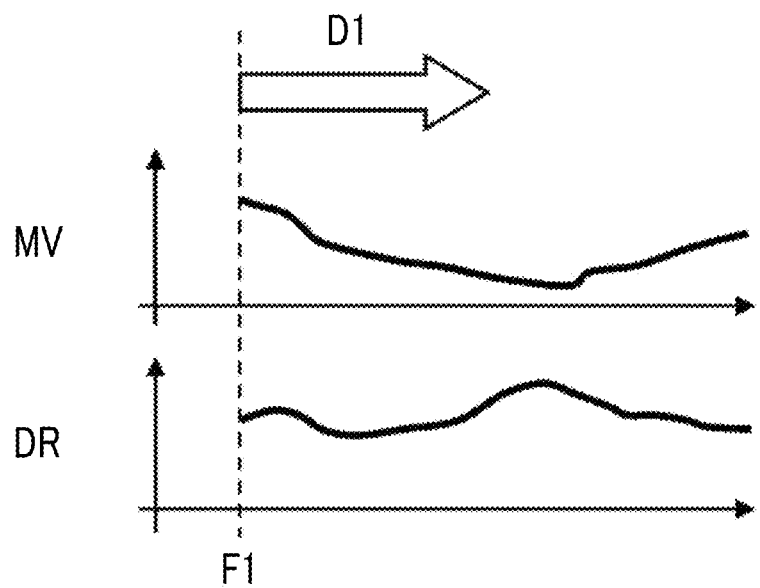
FIG. 19 is a conceptual diagram showing a frame group set as frames to be used for a measurement, in a case where a first measurement frame is positioned in a first half of a plurality of frames in time series in the fourth embodiment of the present invention.

For example, in a case where a frame, among the ultrasound images of the plurality of frames stored in the image memory 9, positioned in the first half of the plurality of frames in time series is set as the first measurement frame F1 by the user through the operation unit 18, the measurement frame selection unit 28 selects a frame group from the first measurement frame F1 to the newest frame among the plurality of frames as a frame group for calculating the measurement value MV and the reliability DR. FIG. 19 is a conceptual diagram showing a frame group selected in this way. In FIG. 19, the measurement value MV and the reliability DR corresponding to each frame are plotted in the order of the frames arranged in time series. In this case, the automatic measurement is performed on each frame of the frame group selected by the measurement frame selection unit 28 in a time series order along the direction D1.

Figure 20:
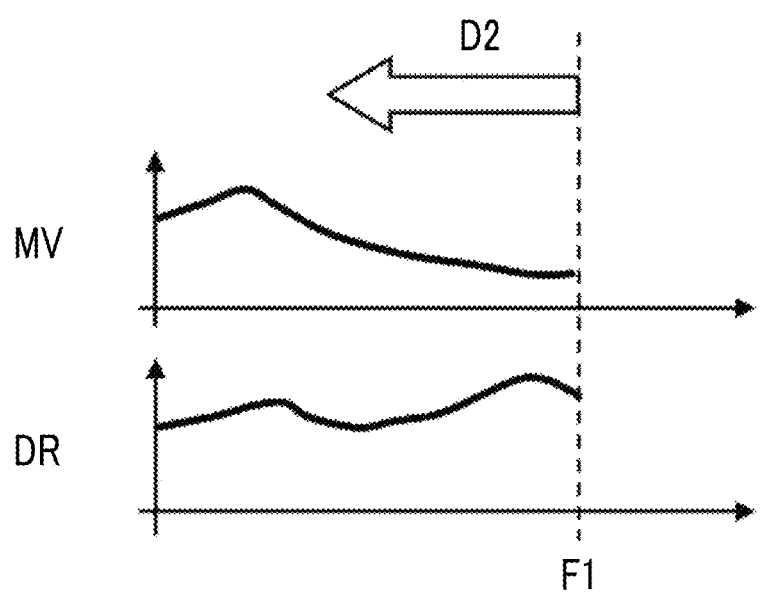
FIG. 20 is a conceptual diagram showing a frame group set as frames to be used for a measurement, in a case where the first measurement frame is positioned in a second half of the plurality of frames in time series in the fourth embodiment of the present invention.

Further, for example, in a case where a frame, among the ultrasound images of the plurality of frames stored in the image memory 9, positioned in the second half of the plurality of frames in time series is set as a first measurement frame F1 by the user through the operation unit 18, the measurement frame selection unit 28 selects a frame group from the oldest frame among the plurality of frames to the first measurement frame F1 as a frame group for calculating the measurement value MV and the reliability DR. FIG. 20 is a conceptual diagram showing a frame group selected in this way. In FIG. 20, similarly to FIG. 19, the measurement value MV and the reliability DR corresponding to each frame are plotted in the order of the frames arranged in time series. In this case, the automatic measurement is performed on each frame of the frame group selected by the measurement frame selection unit 28 in the order of going back in time along the direction D2.

As described above, in a case where the automatic measurement is performed on the frame group selected by the measurement frame selection unit 28, the measurement position setting unit 10 sets the position of the measurement target only for the frame group selected by the measurement frame selection unit 28, and the automatic measurement is performed by the measurement unit 11 with respect to the frame to which the position of the measurement target is set. As a result, the measurement values in the first measurement frame F1 and the second measurement frame F3 are calculated, and the final measurement value is calculated based on these measurement values.

As described above, according to the ultrasound diagnostic apparatus 1C of the fourth embodiment, since a frame group for which the measurement value MV and the reliability DR are calculated can be selected from a plurality of frames stored in the image memory 9, the burden on the ultrasound diagnostic apparatus 1C can be reduced, and the final measurement value can be obtained more quickly.

In the example of the fourth embodiment shown in FIGS. 19 and 20, in a case where a first measurement frame F1 is set by the user through the operation unit 18, the measurement frame selection unit 28 selects a frame group from the first measurement frame F1 to the newest frame or the oldest frame as frames for calculating the measurement value MV and the reliability DR, but, in addition to designation of the first measurement frame F1, the user can designate a measurement end frame for ending the automatic measurement, and the measurement frame selection unit 28 can also select a frame group between the first measurement frame F1 and the measurement end frame as frames for calculating the measurement value MV and the reliability DR.

Figure 21:
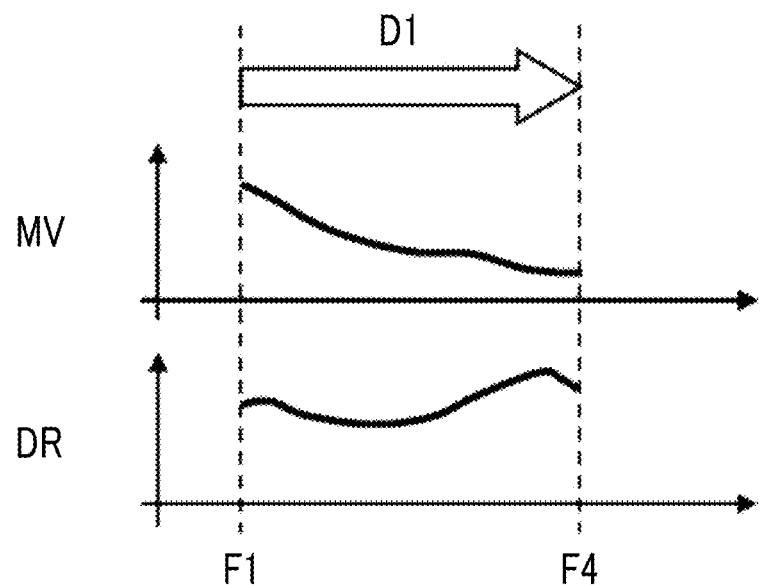
FIG. 21 is a conceptual diagram showing a frame group set as frames to be used for a measurement, in a case where a first measurement frame and a second measurement frame are set before an automatic measurement is performed for a frame in a modification of the fourth embodiment of the present invention.

For example, as shown in FIG. 21, in a case where the measurement end frame F4 for ending the automatic measurement is designated by the user through the operation unit 18, the measurement frame selection unit 28 can select a frame group from the first measurement frame F1 to the measurement end frame F4 designated by the user as the frame group for calculating the measurement value MV and the reliability DR. At this time, although not shown, the user can designate the measurement end frame F4 through the operation unit 18 while referring to the ultrasound images of the plurality of frames displayed in a time series order on the display unit 8, for example, as shown in FIG. 6.

In a case where the frame group for calculating the measurement value MV and the reliability DR is selected in this way, the automatic measurement is performed on the selected frame group in a time series order along the direction D1. In the example shown in FIG. 21, although a newer frame than the first measurement frame F1 in time series is designated as the measurement end frame F4 for ending the automatic measurement, as the measurement end frame F4, an older frame than the first measurement frame F1 in time series may be designated. In that case, the automatic measurement is performed on the selected frame group in the order of going back in time along the direction D2.

As described above, since the frames for performing the automatic measurement can be limited by selecting the measurement end frame F4 for ending the automatic measurement, a burden on the ultrasound diagnostic apparatus 1C is further reduced, and the final measurement value can be obtained more quickly.

Figure 22:
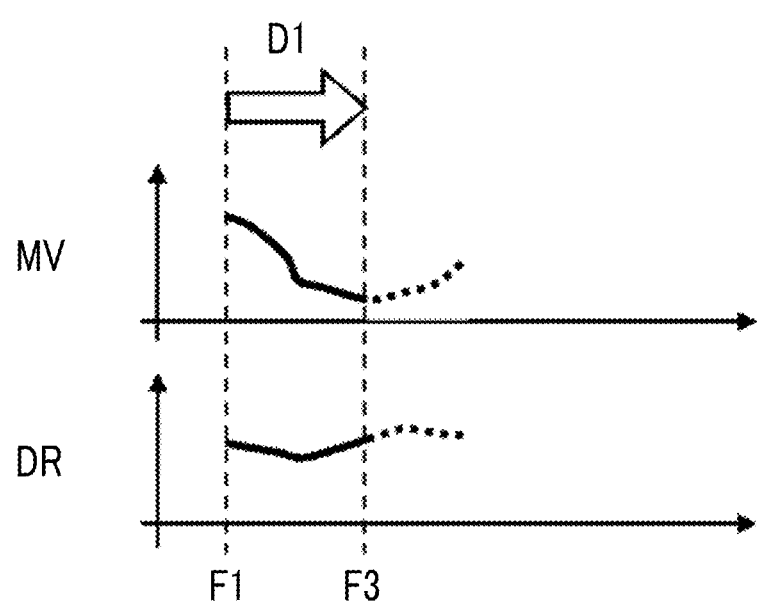
FIG. 22 is a conceptual diagram showing a state where a second measurement frame is set based on a measurement value in another modification of the fourth embodiment of the present invention.

Further, in the process of performing the automatic measurement for the frame group selected by the measurement frame selection unit 28, the second measurement frame F3 can be set. For example, as shown in FIG. 22, in a case where the measurement value MV in the first measurement frame F1 is the maximum value and the automatic measurement is performed for each frame in a time series order in the direction D1, at the time when the measurement value MV becomes the minimum value in the process of performing the automatic measurement, the second measurement frame setting unit 27 can set the frame in which the measurement value MV becomes the minimum value as the second measurement frame F3. Further, at this time, the measurement unit 11 determines that subsequent automatic measurement is unnecessary, and can stop the automatic measurement for each frame in the frame group selected by the measurement frame selection unit 28.

Further, even in a case where the frame group for calculating the measurement value MV and the reliability DR is not selected by the measurement frame selection unit 28, the second measurement frame F3 can be set in the process of performing the automatic measurement for the plurality of frames.

As described above, by setting the second measurement frame F3 in the process of performing the automatic measurement for the plurality of frames, the frame on which the automatic measurement is performed can be omitted, thereby the burden on the ultrasound diagnostic apparatus 1C is further reduced, and the final measurement value can be obtained more quickly.

Fifth Embodiment

In the first to fourth embodiments, although the measurement target is measured for the measurement item that requires a plurality of measurement values V1 for calculating the final measurement value, the ultrasound diagnostic apparatus according to the fifth embodiment can use the measurement value in a single frame as the final measurement value depending on the measurement item. Therefore, the ultrasound diagnostic apparatus according to the fifth embodiment can set whether to calculate the measurement value V1 only for a single frame or to calculate the measurement values V1 in a plurality of frames according to the measurement item.

Here, the ultrasound diagnostic apparatus of the fifth embodiment has the same configuration as that of the ultrasound diagnostic apparatus 1A of the second embodiment shown in FIG. 12. Therefore, the fifth embodiment will be described by using the same reference numerals as those of the ultrasound diagnostic apparatus 1A shown in FIG. 12.

Figure 23:
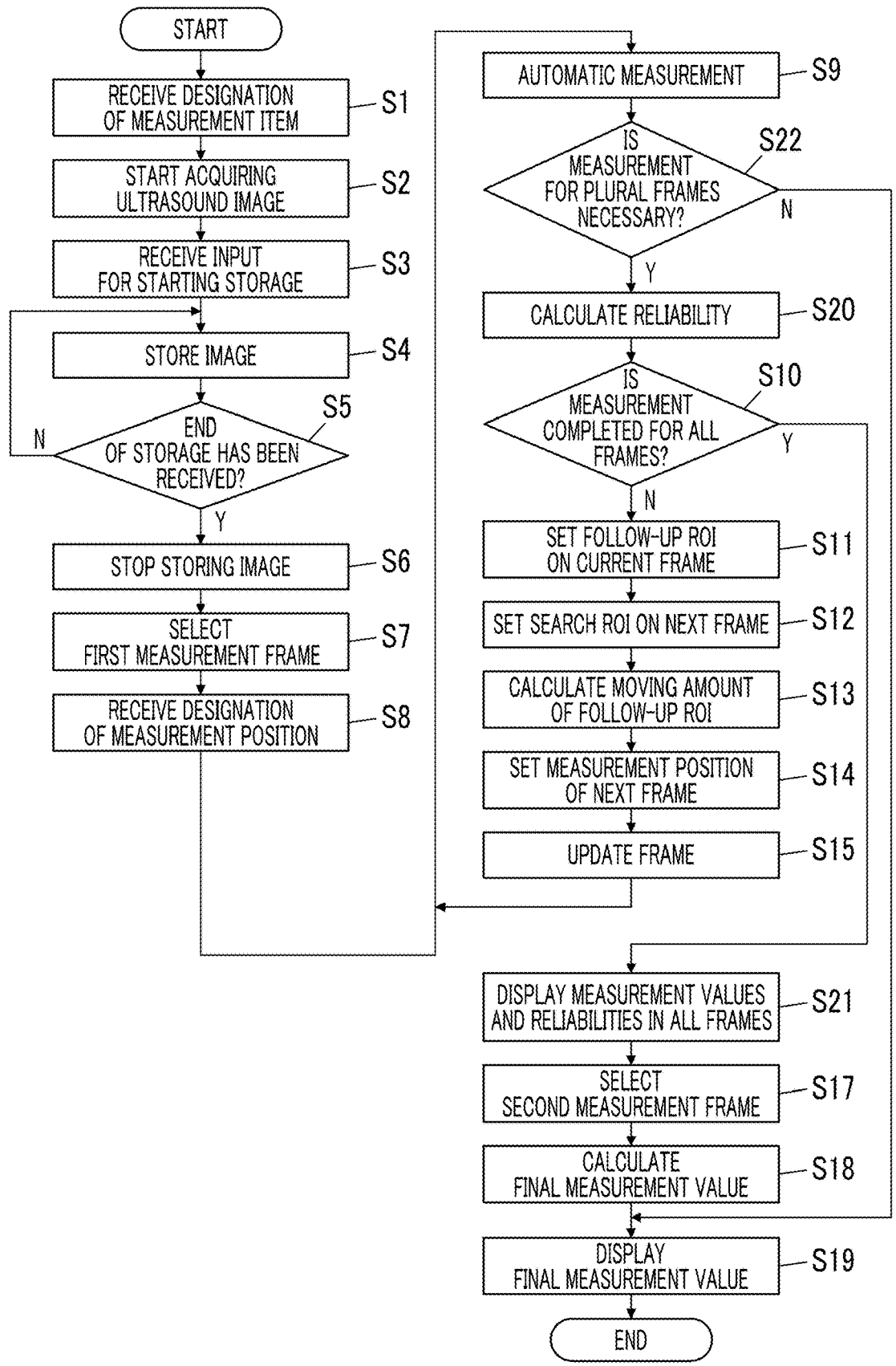
FIG. 23 is a flowchart showing an operation of an ultrasound diagnostic apparatus according to fifth embodiment of the present invention.

FIG. 23 is a flowchart showing an operation of the ultrasound diagnostic apparatus 1A according to the fifth embodiment.

Steps S1 to S9 in FIG. 23 are the same as steps S1 to S9 in the second embodiment shown in FIG. 13. That is, first, in a case where the measurement item designated by the user through the operation unit 18 is received, acquisition of the ultrasound image is started. Next, the ultrasound image acquired from the time when the instruction to start storing the ultrasound image is given by the user through the operation unit 18 to the time when the instruction to end storing the ultrasound image is given is stored in the image memory 9. In a case where the ultrasound images of the plurality of frames are stored in the image memory 9, one frame among the stored plurality of frames is selected as the first measurement frame F1 by the user through the operation unit 18. In a case where the user designates an approximate position of the measurement target with respect to the first measurement frame F1, the automatic measurement of the measurement target is performed on the first measurement frame F1 by the measurement unit 11.

In a case where the automatic measurement for the first measurement frame F1 is performed in step S9, the process proceeds to step S22. In step S22, the device controller 14 determines whether the automatic measurement in the plurality of frames is necessary based on the measurement item designated by the user in step S1. At this time, in a case where the measurement item designated by the user in step S1 is a measurement item that requires the calculation of the final measurement value based on the measurement values V1 in the plurality of frames, such as the inferior vena cava diameter, the process proceeds to step S20.

In this case, the same processing as in step S20, steps S10 to S15, and step S9 in the second embodiment shown in FIG. 13 is performed. That is, in a case where the reliability V2 with respect to the measurement value V1 is calculated in step S20, the processing of steps S10 to S15, step S9, step S22, and step S20 is repeated until the calculation of the measurement value V1 and the reliability V2 is completed for all the frames stored in the image memory 9 in steps S3 to S6. As a result, in a case where it is determined in step S10 that the calculation of the measurement value V1 and the reliability V2 has been completed for all the frames stored in the image memory 9 in steps S3 to S6, and the process proceeds to step S21.

Subsequent steps S21 and S17 to S19 are the same as steps S21 and S17 to S19 in the second embodiment shown in FIG. 13, and all the calculated measurement value V1 and reliability V2 are displayed on the display unit 8, and the final measurement value is calculated, thereby the calculated final measured value is displayed on the display unit 8.

On the other hand, in a case where the measurement item designated by the user in step S1 is a measurement item that requires only measurement in a single frame, such as the kidney and abdominal aorta diameter, in step S22, the device controller 14 determines that the calculation of the reliability V2 and the automatic measurement in a plurality of frames are not necessary, and the process proceeds to step S19.

In step S19, the measurement value V1 calculated in step S9 is displayed as the final measurement value. In this way, the operation of the ultrasound diagnostic apparatus 1A according to the fifth embodiment ends.

As described above, according to the ultrasound diagnostic apparatus 1A of the fifth embodiment, since measurement is performed by automatically determining whether to perform the automatic measurement only for a single frame or to perform the automatic measurement for the plurality of frames according to the measurement item designated by the user, a result suitable for the measurement item can be presented to the user.

EXPLANATION OF REFERENCES

1: ultrasound diagnostic apparatus
2: transducer array
3: transmission unit
4: reception unit
5: AD converter
6: image generation unit
7: display controller
8: display unit
9: image memory
10: measurement position setting unit
11: measurement unit
12: detection measurement algorithm setting unit
13: final measurement value calculation unit
14: device controller
15: measurement item designation receiving unit
16: measurement position designation receiving unit
17: frame designation receiving unit
18: operation unit
19: storage unit
21: ultrasound probe
22: processor
23: signal processing unit
24: DSC
25: image processing unit
26: reliability calculation unit
27: second measurement frame setting unit
28: measurement frame selection unit
A1: measurement value graph
A2: reliability graph
B1: storage start button
B2: storage end button
B3, B4: setting button
D1, D2: direction
DR: reliability
DRth: certain value
E: finger F1: first measurement frame
F2: frame
F3: second measurement frame
F4: measurement end frame
N: list
N1, N2, N3: measurement item
MV1max, MV2max: maximum value
MV1min, MV2min: minimum value
R1: follow-up region of interest
R2: search region of interest
S: range
SB: scroll bar
U, U1, U2, U3, U4, U101, U102, U103, U104: ultrasound image

What is claimed is:

1. An acoustic wave diagnostic apparatus comprising:
an image memory configured to store acoustic wave images of a plurality of frames in time series;
a display configured to display the acoustic wave images;
an input interface for a user configured to perform an input operation; and
a processor,
wherein the processor is configured to
receive a designation of a measurement item related to a measurement target from the user through the input interface,
set a detection measurement algorithm based on the received measurement item,
receive a designation of a first frame among the plurality of frames stored in the image memory from the user through the input interface,
upon receipt of the designation of the first frame, set a subset of frames among the plurality of frames, wherein the subset of frames includes the first frame,
receive a designation of a first position of the measurement target on an acoustic wave image of the first frame,
calculate a movement amount of the acoustic wave images between the subset of frames, and set another position of the measurement target in each of the subset of frames based on the movement amount and the first position of the measurement target,
detect the measurement target and generate a first set of measurement values by measuring the detected measurement target for all of the frames in the subset of frames, based on the first position of the measurement target, the another position of the measurement target and the set detection measurement algorithm, wherein the first set of measurement values includes a first measurement value for the first frame,
select a second measurement value for a second frame in the subset of frames among the first set of measurement values, wherein the second frame of the subset of frames is different from the first frame,
calculate a final measurement value based on the first measurement value for the first frame and the second measurement value for the second frame,
wherein the processor is configured to calculate a reliability of the measurement value for all of the subset of frames and display the calculated reliability on the display, and
the processor is configured to calculate the movement amount by sequentially detecting positions of a follow-up region of interest on adjacent frames among the subset of frames.

2. The acoustic wave diagnostic apparatus according to claim 1,
wherein the second frame is designated by the user through the input interface and received by the processor.

3. The acoustic wave diagnostic apparatus according to claim 2,
wherein the processor is configured to calculate the movement amount by sequentially detecting positions of a follow-up region of interest on adjacent frames among the subset of frames.

4. The acoustic wave diagnostic apparatus according to claim 1,
wherein the processor is configured to automatically set the second frame from among the subset of frames based on the first set of measurement values.

5. The acoustic wave diagnostic apparatus according to claim 4,
wherein in a case where the measurement value in the first frame is a value obtained by measuring one of a maximum value and a minimum value, the processor is configured to select the second measurement value which is the other of the maximum value and the minimum value from the first set of measurement values.

6. The acoustic wave diagnostic apparatus according to claim 5,
wherein the processor is configured to calculate the movement amount by sequentially detecting positions of a follow-up region of interest on adjacent frames among the subset of frames.

7. The acoustic wave diagnostic apparatus according to claim 4,
wherein the processor is configured to calculate the movement amount by sequentially detecting positions of a follow-up region of interest on adjacent frames among the subset of frames.

8. The acoustic wave diagnostic apparatus according to claim 1,
wherein the processor is configured to calculate the movement amount by sequentially detecting positions of a follow-up region of interest on adjacent frames among the subset of frames.

9. The acoustic wave diagnostic apparatus according to claim 1,
wherein the processor is configured to select the subset of frames from the first frame to a newest frame among the plurality of frames as the part of frames in a case where the first frame is positioned in a first half of the plurality of frames in time series, and select the subset of frames from an oldest frame among the plurality of frames to the first frame as the part of frames in a case where the first frame is positioned in a second half of the plurality of frames in time series.

10. The acoustic wave diagnostic apparatus according to claim 1,
wherein the processor is configured to determine whether the received measurement item requests only measurement for a single frame or requests a measurement for a plurality of frames, and in a case of requesting only measurement for the single frame, the processor is configured to display a measurement value for the first frame on the display, and then end the detection and measurement of the measurement target.

11. A control method of an acoustic wave diagnostic apparatus, comprising:
storing acoustic wave images of a plurality of frames continuous in time series;
displaying the acoustic wave images;

receiving a designation of a measurement item related to a measurement target from a user through an input interface;

setting a detection measurement algorithm based on the received measurement item;

receiving a designation of a first frame among the plurality of stored frames from the user through the input interface;

upon receipt of the designation of the first frame, setting a subset of frames among the plurality of frames, wherein the subset of frames includes the first frame, receive a designation of a first position of the measurement target on an acoustic wave image of the first frame, calculating a movement amount of the acoustic wave images between the subset of frames, and setting another position of the measurement target in each of the subset of frames based on the movement amount and the first position of the measurement target;

detecting the measurement target and generating a first set of measurement values by measuring the detected measurement target for all of the frames in the subset of frames, based on the first position of the measurement target, the another position of the measurement target and the set detection measurement algorithm, wherein the first set of measurement values includes a first measurement value for the first frame, selecting a second measurement value for a second frame in the subset of frames among the first set of measurement values, wherein the second frame of the subset of frames is different from the first frame, and calculating a final measurement value based on the first measurement value for the first frame and the second measurement value for the second frame, wherein the processor is configured to calculate a reliability of the measurement value for all of the subset of frames and display the calculated reliability on the display, and the processor is configured to calculate the movement amount by sequentially detecting positions of a follow-up region of interest on adjacent frames among the subset of frames.

12. The control method of an acoustic wave diagnostic apparatus of claim 11, further comprising:

receiving the designation by the user through the input interface.

13. The control method of an acoustic wave diagnostic apparatus of claim 11, wherein the selecting of the second measurement value includes automatically setting the second frame from among the subset of frames based on the first set of measurement values.

14. The control method of an acoustic wave diagnostic apparatus of claim 11, further comprising:

calculating a reliability of the measurement value for all of the subset of frames and display the calculated reliability on the display.

15. The control method of an acoustic wave diagnostic apparatus of claim 14, wherein the selecting of the second measurement value includes automatically setting the second frame from among the subset of frames based on the first set of measurement values and the calculated reliability.

16. The control method of an acoustic wave diagnostic apparatus of claim 11, wherein the calculating the movement amount comprises sequentially detecting positions of a follow-up region of interest on adjacent frames among the subset of frames.

* * * * *